United States Patent [19]
Koopman et al.

[11] Patent Number: 6,143,878
[45] Date of Patent: Nov. 7, 2000

[54] SOX-9 GENE AND PROTEIN AND USE IN THE REGENERATION OF BONE OR CARTILAGE

[75] Inventors: Peter Anthony Koopman, Torwood, Australia; Peter Neville Goodfellow, London, United Kingdom

[73] Assignee: The University of Queensland, St. Lucia, Australia

[21] Appl. No.: 08/860,635

[22] PCT Filed: Nov. 29, 1995

[86] PCT No.: PCT/AU95/00799

§ 371 Date: May 29, 1997

§ 102(e) Date: May 29, 1997

[87] PCT Pub. No.: WO96/17057

PCT Pub. Date: Jun. 6, 1996

[30]     Foreign Application Priority Data

Nov. 29, 1994 [AU]  Australia ................................ PM9714
Dec. 5, 1994 [AU]  Australia ................................ PM9835

[51] Int. Cl.$^7$ ................................................... C07H 21/04
[52] U.S. Cl. .................... 536/23.1; 536/23.5; 435/320.1; 435/69.1; 435/325; 514/44; 424/93.21
[58] Field of Search ..................................... 435/455, 69.1, 435/320.1, 325; 514/44; 530/26.1; 566/23.1, 23.5; 424/93.21

[56]     References Cited

PUBLICATIONS

Chardard et al. (Nucleic Acids Research 21, 15, p. 357), 1993.
Wagner et al. (Cell, vol. 79, pp. 1111–1120), Dec. 1994.
Mundlos et al. (FASEB J., 11, 2, 1997, 125–132), 1997.
Verma et al., Nature, vol. 389, pp. 239–242, 1997.
Gunzburg et al. (Molecular Medicine Today, pp. 410–417, 1995.
Ngo et al., in: The Protein Folding Problem and Tertiary Structure Prediction, 1994, Merz et al., (ed.), Birkhauser, Boston, MA, pp. 433 and 492–494, 1994.
P. Denney et al. (1992) "A conserved family of genes related to the testis determining gene, SRY" *Nucleic Acid Research 20(11):* 2887.
E.M. Wright (1993) "Seven new members of the Sox gene family expressed during mouse development" *Nucleic Acid Research 21(3):* 744.
C. Goze et al. (1993) "Partial Cloning of SOX–11 and SOX–12, two new human SOX genes" *Nucleic Acid Research 21(12):* 2943.
J.W. Foster et al. (1994) "Camponelic dysplasia and autosomal sex reversal caused by mutations in an SRY–related gene" *Nature 372:* 525–530.
E. Wright et al. (1995) "The *Sry*–related gene *Sox9* is expressed during chondrogenesis in mouse embryos" *Nature Genetics 9:* 15–20.
J.R. Hawkins (1995) "Commentary: Genetics of XY sex reversal" *Journal of Endocrinology 147:* 183–187.

*Primary Examiner*—Scott D. Priebe
*Assistant Examiner*—Dave Trong Nguyen
*Attorney, Agent, or Firm*—Scully, Scott, Murphy & Presser

[57]     ABSTRACT

An isolated DNA molecule encoding a Sox-9 gene which codes for the Sox-9 polypeptide. The human Sox-9 gene has been mapped to chromosome 17 in the same region as CMPD-1, the locus for Campomelic Dysplasia (CD). Sox-9 appears to have a role in mammalian skeletal development, and is used in the treatment of diseases involving bond or cartilage deficiency.

4 Claims, 19 Drawing Sheets

(4 of 19 Drawing Sheet(s) Filed in Color)

Mouse Sox9 Sequence

```
   1  AGTTTCAGTC CAGGAACTTT TCTTTGCAAG AGAGACGAGG TGCAAGTGGC
  51  CCCGGTTTCG TTCTCTGTTT TCCCTCCCTC CTCCTCCGCT CCGACTCGCC
 101  TTCCCCGGGT TTAGAGCCGG CAGCTGAGAC CCGCCACCCA GCGCCTCTGC
 151  TAAGTGCCCG CCGCCGCAGC CCGGTGACGC GCCAACCTCC CCGGGAGCCG
 201  TTCGCTCGGC GTCCGCGTCC GGGCAGCTGA GGGAAGAGGA GCCCCAGCCG
 251  CCGCGGCTTC TCGCCTTTCC CGGCCACCCG CCCCTGCCC CGGGCTCGCG
 301  TATGAATCTC CTGGACCCCT TCATGAAGAT GACCGACGAG CAGGAGAAGG
 351  GCCTGTCTGG CGCCCCCAGC CCCACCATGT CGGAGGACTC GGCTGGTTCG
 401  CCCTGTCCCT CGGGCTCCGG CTCGGACACG GAGAACACCC GGCCCCAGGA
 451  GAACACCTTC CCCAAGGGCG AGCCGGATCT GAAGAAGGAG AGCGAGGAAG
 501  ATAAGTTCCC CGTGTGCATC CGCGAGGCGG TCAGCCAGGT GCTGAAGGGC
 551  TACGACTGGA CGCTGGTGCC CATGCCCGTG CGCGTCAACG GCTCCAGCAA
 601  GAACAAGCCA CACGTCAAGC GACCCATGAA CGCCTTCATG GTGTGGGCGC
 651  AGGCTGCGCG CAGGAAGCTG GCAGACCAGT ACCCGCATCT GCACAACGCG
 701  GAGCTCAGCA AGACTCTGGG CAAGCTCTGG AGGCTGCTGA ACGAGAGCGA
 751  GAAGAGACCC TTCGTGGAGG AGGCGGAGCG GCTGCGCGTG CAGCACAAGA
 801  AAGACCACCC CGATTACAAG TACCAGCCCC GGCGGAGGAA GTCGGTGAAG
 851  AACGGACAAG CGGAGGCCGA AGAGGCCACG GAACAGACTC ACATCTCTCC
 901  TAATGCTATC TTCAAGGCGC TGCAAGCCGA CTCCCCACAT TCCTCCTCCG
 951  GCATGAGTGA GGTGCACTCC CCGGGCGAGC ACTCTGGGCA ATCTCAGGGT
1001  CCGCCGACCC CACCCACCAC TCCCAAAACC GACGTGCAAG CTGGCAAAGT
1051  TGATCTGAAG CGAGAGGGGC GCCCTCTGGC AGAGGGGGC AGACAGCCCC
1101  CCATCGACTT CCGCGACGTG GACATCGGTG AACTGAGCAG CGACGTCATC
1151  TCCAACATTG AGACCTTCGA CGTCAATGAG TTTGACCAAT ACTTGCCACC
1201  CAACGGCCAC CCAGGGGTTC CGGCCACCCA CGGCCAGGTC ACCTACACTG
1251  GCAGTTACGG CATCAGCAGC ACCGCACCCA CCCCTGCGAC CGCGGGCCAC
```

Figure 1(a)

```
1301  GTGTGGATGT CGAAGCAGCA GGCGCCGCCC CCTCCTCCGC AGCAGCCTCC

1351  GCAGGCCCCG CAAGCCCCAC AGGCGCCTCC GCAGCAGCAA GCACCCCCGC

1401  AGCAGCCGCA GGCACCCCAG CAGCAGCAGG CACACACGCT CACCACGCTG

1451  AGCAGCGAGC CAGGCCAGTC CCAGCGAACG CACATCAAGA CGGAGCAGCT

1501  GAGCCCCAGC CACTACAGGG AGCAGCAGCA GCACTCCCCG CAACAGATCT

1551  CCTACAGCCC CTTCAACCTT CCTCACTACA GGCCCTCCTA CCCGCCCATC

1601  ACCCGTTCGG AATACGACTA CGCTGACCAT CAGAACTCCG GCTCCTACTA

1651  CAGTCACGCA GCCGGCCAGG GCTCAGGGCT CTACTCCACC TTCACTTACA

1701  TGAACCCCGC GCAGCGCCCC ATGTACACCC CCATCGGTGA CACCTCCGGG

1751  GTCCCTTCCA TCCCGCAGAC CCACAGCCCG CAGGACTGGG AACAACCAGT

1801  CTACACACAG GTCACCAGAC CCTGAGAAGA GAAAAGCTAT GGTGACAGAG

1851  CTGATCTTTT TTTTTTTTTT TTTTTAAAGA AGAAAAGAAA GAAACGAAAA

1901  AGAAAAAGCT GAAGGAAATC AAGAACCAAT TGAAATTCCT TTGGACACTT

1951  TTTTTTTTGT CCTTTCGTTA ATTTTAAAA GACATGTAAA GGAAGGTAAC

2001  GATTGCTGGG CATTCCAGGA GAGAGACTTT AAGACTTTGT CTGAGCTCAT

2051  GACAACATAT TGCAAATGGC CGGGCCACTC GTGGCCAGAC GGACAGCACT

2101  CCTGGCCAGA TGGACCCACC AGTATCAGCG AGGAGGGGCT TGTCTCCTTC

2151  AGAGTTAACA TGGAGGACGA TTGGAGAATC TCCCTGCCTG TTTGGACTTT

2201  GTAATTATTT TTTAGCCGTA ATTAAAGAAA AAAAAAGTCC AAAAAAAAA
```

Figure 1(b)

Mouse Sox-9 amino acid sequence

```
Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
            20                  25                  30

Ser Pro Cys Pro Ser Gly Ser Gly Ser Asp Thr Glu Asn Thr Arg Pro
            35                  40                  45

Gln Glu Asn Thr Phe Pro Lys Gly Glu Pro Asp Leu Lys Lys Glu Ser
    50                  55                  60

Glu Glu Asp Lys Phe Pro Val Cys Ile Arg Glu Ala Val Ser Gln Val
65                  70                  75                  80

Leu Lys Gly Tyr Asp Trp Thr Leu Val Pro Met Pro Val Arg Val Asn
                85                  90                  95

Gly Ser Ser Lys Asn Lys Pro His Val Lys Arg Pro Met Asn Ala Phe
            100                 105                 110

Met Val Trp Ala Gln Ala Ala Arg Arg Lys Leu Ala Asp Gln Tyr Pro
            115                 120                 125

His Leu His Asn Ala Glu Leu Ser Lys Thr Leu Gly Lys Leu Trp Arg
    130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
                165                 170                 175

Arg Arg Arg Lys Ser Val Lys Asn Gly Gln Ala Glu Ala Glu Glu Ala
            180                 185                 190

Thr Glu Gln Thr His Ile Ser Pro Asn Ala Ile Phe Lys Ala Leu Gln
            195                 200                 205

Ala Asp Ser Pro His Ser Ser Ser Gly Met Ser Glu Val His Ser Pro
    210                 215                 220

Gly Glu His Ser Gly Gln Ser Gln Gly Pro Pro Thr Pro Pro Thr Thr
225                 230                 235                 240

Pro Lys Thr Asp Val Gln Ala Gly Lys Val Asp Leu Lys Arg Glu Gly
                245                 250                 255

Arg Pro Leu Ala Glu Gly Gly Arg Gln Pro Pro Ile Asp Phe Arg Asp
            260                 265                 270
```

Figure 1(c)

Val Asp Ile Gly Glu Leu Ser Ser Asp Val Ile Ser Asn Ile Glu Thr
            275                 280                 285

Phe Asp Val Asn Glu Phe Asp Gln Tyr Leu Pro Pro Asn Gly His Pro
        290                 295                 300

Gly Val Pro Ala Thr His Gly Gln Val Thr Tyr Thr Gly Ser Tyr Gly
305                         310                 315                 320

Ile Ser Ser Thr Ala Pro Thr Pro Ala Thr Ala Gly His Val Trp Met
                325                 330                 335

Ser Lys Gln Gln Ala Pro Pro Pro Pro Gln Gln Pro Pro Gln Ala
            340                 345                 350

Pro Gln Ala Pro Gln Ala Pro Pro Gln Gln Gln Ala Pro Pro Gln Gln
        355                 360                 365

Pro Gln Ala Pro Gln Gln Gln Ala His Thr Leu Thr Thr Leu Ser
        370                 375                 380

Ser Glu Pro Gly Gln Ser Gln Arg Thr His Ile Lys Thr Glu Gln Leu
385                 390                 395                 400

Ser Pro Ser His Tyr Arg Glu Gln Gln His Ser Pro Gln Gln Ile
            405                 410                 415

Ser Tyr Ser Pro Phe Asn Leu Pro His Tyr Arg Pro Ser Tyr Pro Pro
            420                 425                 430

Ile Thr Arg Ser Glu Tyr Asp Tyr Ala Asp His Gln Asn Ser Gly Ser
            435                 440                 445

Tyr Tyr Ser His Ala Ala Gly Gln Gly Ser Gly Leu Tyr Ser Thr Phe
        450                 455                 460

Thr Tyr Met Asn Pro Ala Gln Arg Pro Met Tyr Thr Pro Ile Gly Asp
465                 470                 475                 480

Thr Ser Gly Val Pro Ser Ile Pro Gln Thr His Ser Pro Gln Asp Trp
            485                 490                 495

Glu Gln Pro Val Tyr Thr Gln Val Thr Arg Pro
            500                 505

Figure 1(d)

```
CGGAGCTCGA AACTGACTGG AAACTTCAGT GGCGCGGAGA CTCGCCAGTT TCAACCCCGG
AAACTTTTCT TTGCAGGAGG AGAAGAGAAG GGGTGCAAGC GCCCCCACTT TTGCTCTTTT
TCCTCCCCTC CTCCTCCTCT CCAATTCGCC TCCCCCCACT TGGAGCGGGC AGCTGTGAAC
TGGCCACCCC GCGCCTTCCT AAGTGCTCGC CGCGGTAGCC GGCCGACGCG CCAGCTTCCC
CGGGAGCCGC TTGCTCCGCA TCCGGGCAGC CGAGGGGAGA GGAGCCCGCG CCTCGAGTCC
CCGAGCCGCC GCGGCTTCTC GCCTTTCCCG GCCACCAGCC CCTGCCCCG GGCCCGCGTA
TGAATCTCCT GGACCCCTTC ATGAAGATGA CCGACGAGCA GGAGAAGGGC CTGTCCGGCG
CCCCCAGCCC CACCATGTCC GAGGACTCCG CGGGCTCGCC CTGCCCGTCG GGCTCCGGCT
CGGACACCGA GAACACGCGG CCCCAGGAGA ACACGTTCCC CAAGGGCGAG CCCGATCTGA
AGAAGGAGAG CGAGGAGGAC AAGTTCCCCG TGTGCATCCG CGAGGCGGTC AGCCAGGTGC
TCAAAGGCTA CGACTGGACG CTGGTGCCCA TGCCGGTGCG CGTCAACGGC TCCAGCAAGA
ACAAGCCGCA CGTCAAGCGG CCCATGAACG CCTTCATGGT GTGGGCGCAG GCGGCGCGCA
GGAAGCTCGC GGACCAGTAC CCGCACTTGC ACAACGCCGA GCTCAGCAAG ACGCTGGGCA
AGCTCTGGAG ACTTCTGAAC GAGAGCGAGA AGCGGCCCTT CGTGGAGGAG GCGGAGCGGC
TGCGCGTGCA GCACAAGAAG GACCACCCGG ATTACAAGTA CCAGCCGCGG CGGAGGAAGT
CGGTGAAGAA CGGGCAGGCG GAGGCAGAGG AGGCCACGGA GCAGACGCAC ATCTCCCCCA
ACGCCATCTT CAAGGCGCTG CAGGCCGACT CGCCACACTC CTCCTCCGGC ATGAGCGAGG
TGCACTCCCC CGGCGAGCAC TCGGGGCAAT CCCAGGGCCC ACCGACCCCA CCCACCACCC
CCAAAACCGA CGTGCAGCCG GGCAAGGCTG ACCTGAAGCG AGAGGGGCGC CCCTTGCCAG
AGGGGGGCAG ACAGCCCCCT ATCGACTTCC GCGACGTGGA CATCGGCGAG CTGAGCAGCG
ACGTCATCTC CAACATCGAG ACCTTCGATG TCAACGAGTT TGACCAGTAC CTGCCGCCCA
ACGGCCACCC GGGGGTGCCG GCCACGCACG GCCAGGTCAC CTACACGGGC AGCTACGGCA
TCAGCAGCAC CGCGGCCACC CCGGCGAGCG CGGGCCACGT GTGGATGTCC AAGCAGCAGG
CGCCGCCGCC ACCCCCGCAG CAGCCCCCAC AGGCCCCGCC GGCCCCGCAG GCGCCCCCGC
AGCCGCAGGC GGCGCCCCCA CAGCAGCCGG CGGCACCCCC GCAGCAGCCA CAGGCGCACA
CGCTGACCAC GCTGAGCAGC GAGCCGGGCC AGTCCCAGCG AACGCACATC AAGACGGAGC
AGCTGAGCCC CAGCCACTAC AGCGAGCAGC AGCAGCACTC GCCCCAACAG ATCGCCTACA
GCCCCTTCAA CCTCCCACAC TACAGCCCCT CCTACCCGCC CATCACCCGC TCACAGTACG
ACTACACCGA CCACCAGAAC TCCAGCTCCT ACTACAGCCA CGCGGCAGGC CAGGGCACCG
GCCTCTACTC CACCTTCACC TACATGAACC CCGCTCAGCG CCCCATGTAC ACCCCCATCG
CCGACACCTC TGGGGTCCCT TCCATCCCGC AGACCCACAG CCCCCAGCAC TGGGAACAAC
CCGTCTACAC ACAGCTCACT CGACCTTGAG GAGGCCTCCC ACGAAGGGCG ACGATGGCCG
AGATGATCCT AAAAATAACC GAAGAAAGAG AGGACCAACC AGAATTCCCT TTGGACATTT
GTGTTTTTTT GTTTTTTTAT TTTGTTTTGT TTTTCTTCT TCTTCTTCTT CCTTAAAGAC
ATTTAAGCTA AAGGCAACTC GTACCCAAAT TTCCAAGACA CAAACATGAC CTATCCAAGC
GCATTACCCA CTTGTGGCCA ATCAGTGGCC AGGCCAACCT TGGCTAAATG GAGCAGCGAA
ATCAACGAGA AACTGGACTT TTTAAACCCT CTTCAGAGCA AGCGTGGAGG ATGATGGAGA
ATCGTGTGAT CAGTGTGCTA AATCTCTCTG CCTGTTTGGA CTTTGTAATT ATTTTTTTAG
CAGTAATTAA AGAAAAAAGT CCTCTGTGAG GAATATTCTC TATTTTAAAT ATTTTTAGTA
TGTACTGTGT ATGATTCATT ACCATTTTGA GGGGATTTAT ACATATTTTT AGATAAAATT
AAATGCTCTT ATTTTTCCAA CAGCTAAACT ACTCTTAGTT GAACAGTGTG CCCTAGCTTT
TCTTGCAACC AGAGTATTTT TGTACAGATT TGCTTTCTCT TACAAAAAGA AAAAAAAAT
CCTGTTGTAT TAACATTTAA AAACAGAATT GTGTTATGTG ATCAGTTTTG GGGGTTAACT
TTGCTTAATT CCTCAGGCTT TGCGATTTAA GGAGGAGCTG CCTTAAAAAA AAATAAAGGC
CTTATTTTGC AATTATGGGA GTAAACAATA GTCTAGAGAA GCATTGGTA AGCTTTATGA
TATATATATT TTTTAAAGAA GAGAAAACA CCTTGAGCCT TAAAACGGTG CTGCTGGGAA
ACATTTGCAC TCTTTTAGTG CATTTCCTCC TGCCTTTGCT TGTTCACTGC AGTCTTAAGA
AAGAGGTAAA AGGCAAGCAA AGGAGATGAA ATCTGTTCTG GAATGTTTC AGCAGCCAAT
AAGTGCCCGA GCACACTGCC CCCGGTTGCC TGCCTGGGCC CCATGTGGAA GGCAGATGCC
TGCTCGCTCT GTCACCTGTG CCTCTCAGAA CACCAGCAGT TAACCTTCAA GACATTCCAC
```

Figure 8a (i)

```
TTGCTAAAAT TATTTATTTT GTAAGGAGAG GTTTTAATTA AAACAAAAAA AAATTCTTTT
TTTTTTTTTT TTTTCCAATT TTACCTTCTT TAAAATAGGT TGTTGGAGCT TTCCTCAAAG
GGTATGGTCA TCTGTTGTTA AATTATGTTC TTAACTGTAA CCAGTTTTTT TTTATTTATC
TCTTTAATCT TTTTTATTAT TAAAAGCAAG TTTCTTTGTA TTCCTCACCC TAGATTTGTA
TAAATGCCTT TTTGTCCATC CCTTTTTTCT TTGTTGTTTT TGTTGAAAAC AAACTGGAAA
CTTGTTTCTT TTTTTGTATA AATGAGAGAT TGCAAATGTA GTGTATCACT GAGTCATTTG
CAGTGTTTTC TGCCACAGAC CTTTGGGCTG CCTTATATTG TGTGTGTGTG TGGGTGTGTG
TGTGTTTTGA CACAAAAACA ATGCAAGCAT GTGTCATCCA TATTTCTCTA CATCTTCTCT
TGGAGTGAGG GAGGCTACCT GGAGGGGATC AGCCCACTGA CAGACCTTAA TCTTAATTAC
TGCTGTGGCT AGAGAGTTTG AGGATTGCTT TTTAAAAAAG ACAGCAAACT TTTTTTTTTA
TTTAAAAAAA GATATATTAA CAGTTTTAGA AGTCAGTAGA ATAAAATCTT AAAGCACTCA
TAATATGGCA TCCTTCAATT TCTGTATAAA AGCAGATCTT TTTAAAAAAG ATACTTCTGT
AACTTAAGAA ACCTGGCATT TAAATCATAT TTTGTCTTTA GGTAAAAGCT TTGGTTTGTG
TTCGTGTTTT GTTTGTTTCA CTTGTTTCCC TCCCAGCCCC AAACCTTTTG TTCTCTCCGT
GAAACTTACC TTTCCTTTTT TCTTTCTCTT TTTTTTTTTG TATATTATTG TTTACAATAA
ATATACATTG CATTAAAAAG AAA
```

Figure 8a (ii)

```
Met Asn Leu Leu Asp Pro Phe Met Lys Met Thr Asp Glu Gln Glu Lys
 1            5                   10                  15
Gly Leu Ser Gly Ala Pro Ser Pro Thr Met Ser Glu Asp Ser Ala Gly
             20              25              30
Ser Pro Cys Pro Ser Gly Ser Gly Ser Asp Thr Glu Asn Thr Arg Pro
         35                  40                  45
Gln Glu Asn Thr Phe Pro Lys Gly Glu Pro Asp Leu Lys Lys Glu Ser
     50                  55                  60
Glu Glu Asp Lys Phe Pro Val Cys Ile Arg Glu Ala Val Ser Gln Val
 65                  70                  75                  80
Leu Lys Gly Tyr Asp Trp Thr Leu Val Pro Met Pro Val Arg Val Asn
             85                  90                  95
Gly Ser Ser Lys Asn Lys Pro His Val Lys Arg Pro Met Asn Ala Phe
             100                 105                 110
Met Val Trp Ala Gln Ala Ala Arg Arg Lys Leu Ala Asp Gln Tyr Pro
         115                 120                 125
His Leu His Asn Ala Glu Leu Ser Lys Thr Leu Gly Lys Leu Trp Arg
     130                 135                 140
Leu Leu Asn Glu Ser Glu Lys Arg Pro Phe Val Glu Glu Ala Glu Arg
145                 150                 155                 160
Leu Arg Val Gln His Lys Lys Asp His Pro Asp Tyr Lys Tyr Gln Pro
             165                 170                 175
Arg Arg Arg Lys Ser Val Lys Asn Gly Gln Ala Glu Ala Glu Glu Ala
             180                 185                 190
Thr Glu Gln Thr His Ile Ser Pro Asn Ala Ile Phe Lys Ala Leu Gln
     195                 200                 205
Ala Asp Ser Pro His Ser Ser Ser Gly Met Ser Glu Val His Ser Pro
     210                 215                 220
Gly Glu His Ser Gly Gln Ser Gln Gly Pro Pro Thr Pro Pro Thr Thr
225                 230                 235                 240
Pro Lys Thr Asp Val Gln Pro Gly Lys Ala Asp Leu Lys Arg Glu Gly
             245                 250                 255
Arg Pro Leu Pro Glu Gly Gly Arg Gln Pro Pro Ile Asp Phe Arg Asp
             260                 265                 270
Val Asp Ile Gly Glu Leu Ser Ser Asp Val Ile Ser Asn Ile Glu Thr
         275                 280                 285
Phe Asp Val Asn Glu Phe Asp Gln Tyr Leu Pro Pro Asn Gly His Pro
     290                 295                 300
Gly Val Pro Ala Thr His Gly Gln Val Thr Tyr Thr Gly Ser Tyr Gly
305                 310                 315                 320
Ile Ser Ser Thr Ala Ala Thr Pro Ala Ser Ala Gly His Val Trp Met
             325                 330                 335
Ser Lys Gln Gln Ala Pro Pro Pro Pro Gln Gln Pro Pro Gln Ala
     340                 345                 350
Pro Pro Ala Pro Gln Ala Pro Pro Gln Pro Gln Ala Ala Pro Pro Gln
     355                 360                 365
Gln Pro Ala Ala Pro Pro Gln Gln Pro Gln Ala His Thr Leu Thr Thr
370                 375                 380
```

Figure 8a (iii)

```
Leu Ser Ser Glu Pro Gly Gln Ser Gln Arg Thr His Ile Lys Thr Glu
385             390                 395                 400
Gln Leu Ser Pro Ser His Tyr Ser Glu Gln Gln His Ser Pro Gln
            405                 410             415
Gln Ile Ala Tyr Ser Pro Phe Asn Leu Pro His Tyr Ser Pro Ser Tyr
            420             425                 430
Pro Pro Ile Thr Arg Ser Gln Tyr Asp Tyr Thr Asp His Gln Asn Ser
            435                 440             445
Ser Ser Tyr Tyr Ser His Ala Ala Gly Gln Gly Thr Gly Leu Tyr Ser
    450             455                 460
Thr Phe Thr Tyr Met Asn Pro Ala Gln Arg Pro Met Tyr Thr Pro Ile
465             470                 475                 480
Ala Asp Thr Ser Gly Val Pro Ser Ile Pro Gln Thr His Ser Pro Gln
            485                 490             495
His Trp Glu Gln Pro Val Tyr Thr Gln Leu Thr Arg Pro
            500             505
```

Figure 8a (iv)

SOX-9 GENE AND PROTEIN AND USE IN THE REGENERATION OF BONE OR CARTILAGE

THIS INVENTION relates to the Sox-9(SOX-9 in humans) gene which appears to have a role in mammalian skeletal development and which is also related to the inherited skeletal disease syndrome Campomalic Dysplasia (CD), alternatively known as campomelic dwarfism or campomelic syndrome.

FIELD OF THE INVENTION

CD is an osteochondrodysplasia affecting 0.05–2.2 per 10,000 live births. It is characterised by congenital bowing and angulation of the long bones, together with other skeletal defects, The scapulae are very small and the pelvis and the spine show changes. One pair of ribs is usually missing. Severe anomalies of the lower cervical spine are seen. The interior part of the scapula is hypoplastic. Cleft palate, micrognethia, flat face and hypertension are also features. Various defects of the ear have been noted, affecting the cochlea, malleus, incus, stapes and tympanum. Most patients die in the neonatal period of respiratory distress which has been attributed to hypoplsia of tracheobronchial cartilage (Lee et al., 1972, Am. J. Dis. Child, 124, 485–496) and small thoracic cage (Houston et al., 1983, Am. J. Med. Genet., 15, 3–28).

The human SOX-9 gene has been mapped to chromosome 17 within a region which also contains CMPD1, the locus for CD.

Chromosomal localisation of CMPD1 was based on three independent, apparently balanced, de novo reciprocal translocation involving chromosome 17 (Tommerup et al., 1993, Nature Genet., 4, 170–174). All three translocations had breakpoints between 17q24 and q25, distal to the growth hormone locus (GH) but proximal to thymidine kinase (TK-1). This mapping excluded previous CMPD1 candidates HOX2 and COL1A1. Mutations within the SOX-9 gene have now been found in DNA from CD patients (Foster et al., Nature, in press; Wagner et al., Cell, in press) proving that the SOX-9 gene has a role in skeletal development. Curiously, CD is often associated with sex reversal (Hovmoller et al., 1977, Hereditas, 86, 51–62). Among 33 cases with CD and an XY karyotype, 21 were phenotypic females and two were intersexes (Houston et al., 1983, supra). This association defines an autosomal sex-reversal locus SRA1 at or near the CMPD1 locus.

Recurrent observations of CD in sibs and occasional consanguinity in CD-affected families have led to the belief that CD is inherited as an autosomal recessive disorder. However, a total of five independent de novo chromosomal rearrangements associated with CD lends some support to a dominant, usually lethal mutation (Tommerup et al., 1993, supra). This may explain a case of CD affecting a mother and daughter, although it is possible that the milder phenotype in these patients represents a different mutation (Lynch et al., 1993, J. Med. Genet., 30, 683–686).

The murine Sox-9 gene has been mapped to distal mouse chromosome 11. This region contains various disease loci including Ts, the locus for the mouse mutant Tail-short.

Tommerup et al., 1993, above, have noted the similarities between CD and Tail-short (Ts), which also maps between Gh and Tk-1 of mouse chromosome 11 (Buchberg et al., 1992, Mammal, Genome, 3, 5162–181). No sex reversal has been associated with Ts. It is not yet clear whether the same gene is affected in both CD and Tail-short. The similarity between the two phenotypes raises the intriguing possibility that the human mutation would be homozygous lethal at the blastocyst stage, with heterozygosity resulting in the campomelic phenotype.

Ts is a mouse developmental mutant first described by Morgan, 1950, J. Hered., 41, 208–215. The mutation is semi-dominant: homozygotes die at the blastocyst stage, before or shortly after implantation (Paterson, 1980, J. Expt. Zool., 211, 247–256). Heterozygotes are small with kinked tails and numerous other skeletal defects. The phenotype is variable, but typical abnormalities have been described (Deol, 1961, Proc. R. Soc. Lon. B., 155, 78–95). The short, kinked tail is caused by reduced number and dysmorphology of caudal vertebrae. Vertebral fusions and dyssymphyses also affect the presacral and sacral regions. The humerus, tibia, and to a lesser extent femur and radius are affected by shortening and in some cases bending. Anomalies of the feet are common. These include triphalangy of digit I, absence of falciform, and various digital and other fusions. Additional ribs and rib fusions, and various skull abnormalities are evident.

Despite the obvious effects on the skeletal system in Tail-short and CD, there is some debate as to the nature of the primary defect. Ts is associated with anaemia and general growth retardation appearing at day 9, two days before the first signs of skeletal abnormality appear (Deol, 1961, above). CD is associated with vascular defects and aberrant musculature (Rodiguez, 1993, Am. J. Med. Genet., 46, 185–192) and has been mimicked in avian and amphibian embryos by teratogens affecting the nervous system (Roth, 1991, Paedr. Radiol., 21, 220–225).

SOX-9 encodes one of a family of transcription factors related to the mammalian Y-linked testis determining factor Sry. The cloning of the Y-linked testis determining gene (SRY in humane, Sry in mice) in 1990 (Gubbay et al., 1990, Nature, 346, 245–250; Sinclair et al., 1990, Nature, 346, 240–244) and subsequent demonstration that its expression is sufficient to cause male development in chromosonally female (XX) mice (Koopman et al., 1991, Sry. Nature, 351, 117–121) represented a breakthrough in positional cloning and developmental biology. The protein product of Sry contains a 79 amino acid motif that had already been detected in several other proteins, notably the high mobility group (HMG) of nuclear proteins (Jantzen et al., 1990, Nature, 344, 830–836), Several known sequence-specific DNA binding proteins contain a similar motif. Recent evidence that SRY can bind directly to DNA in a sequence-specific manner (Giese et al., 1992, Science, 255, 453–456) supports the contention that Sry acts as a transcription factor.

When a probe corresponding to the HMG box region of human SRY was hybridised to Southern blots of mouse DNA, a large number of bands was seen in addition to the strongly hybridising, Y-specific band representing mouse Sry (Gubbay et al., 1990, supra). These additional bands are present in both XX female and XY male, DNA, suggesting that there are genes related to Sry by the HMG box, present on autosomes and/or the X chromosome. Indeed, screening of cDNA libraries with an HMG box probe derived from Sry yielded four classes of hybridising clone, none of them Y-linked. Sequencing of these clones showed that they are highly related to each other (78–98% amino acid homology in the HMG box region) as well as to Sry (77–82%). They are less closely related to other mammalian genes containing HMG boxes (around 50% amino acid homology in the HMG box region). These non-Y-linked homologues of Sry have been named Sox genes (Sry-type HMG box genes). Together with Sry, the Sox genes represent a distinct family of mouse genes that appear to encode transcription factors. Western blotting using an antibody to the SRY HMG box suggests that the number of SOX genes may be as high as 50.

cDNA clones corresponding to genes dubbed Sox-1 to -4 were isolated from an 8.5 days post coitum (dpc) mouse embryo library (Gubbay et al., 1990, supra), raising speculation that they play a role in developmental decisions in the mammalian embryo. These genes were expressed throughout the CNS at first, and later become restricted to subsets of nervous tissue such as the developing eye and ear. It appears that Sox-1 to -3 are involved in specifying the development of the central nervous system. Sox-4 acts as a transcriptional activator in T-lymphocytes (van de Wetering et al., 1993, EMBO J., 12, 3847–3854). Sox-5 is expressed stage-specifically in round spermatids in the adult testis, suggesting a role in permatogenesis, and was also shown to bind DNA in vitro (Denny et al., 1992, EMBO J., 11, 3705–3712). Denny et al., 1992, Nucleic Acids Res., 20, 2887, identified two further Sox sequences. Sox-6 and Sox-7, but corresponding cDNAs have yet to be cloned and their expression has not been characterised.

A further 10 members of the mouse Sox gene family have been identified. Degenerate primers were made corresponding to highly conserved regions at the ends of the HMG box of Sry and known Sox genes. Total RNA was prepared from 11.5 days post coitum (dpc) mouse embryos and reverse transcriptase polymerase chain reaction (RT-PCR) was performed using the degenerate primers. The PCR products were cloned and sequenced to reveal seven novel genes which have been called Sox-8, -9, -10, -11, -12, -13 and -14 (Wright et al., 1993, Nucleic Acids Res., 21, 744). Three more Sox sequences have also been isolated (Sox-16, -17 and -18) from macrophage and muscle cDNA (Layfield et al., unpublished data). Sequence comparison of the mouse Sox gene family in regard to the HMG box indicates that the Sox genes fall into seven distinct sub-groups; A: Sry; B: Sox-1, -2, -3 and -14; C: Sox-4, -11 and -12; D: Sox-5, -6 and -13; E: Sox-8, -9 and -10; F: Sox-7, -17 and -18; G: Sox-15 and -16. Whether this structural sub-grouping is reflected in the functions of these genes remains to be determined, but there is every indication that Sox genes represent a major development gene family, similar in many respects to the Hox and Pax families of developmental genes.

The conclusion that Sox genes play an important role in development is reinforced by the finding that multiple Sox genes are present in the genomes of many non-mammalian species. Six Sry-related sequences have been described in the lesser black-backed gull *Larus fuscus*, nine in American alligator, five in lizards, eight in chickens, seven in Drosophila and three in frogs (Griffiths, 1991, Phil. Trans. Roy. Soc. Lond. B., 244, 123–128; Denny et al., 1992, Nucleic Acids Res. above, Coriat et al., 1993, PCR Meth. App., 2, 218–222). Sox genes are widespread within the class mammalia. Sox-3 was recently cloned in marsupials (Foster and Graves, 1994, Proc. Natl. Acad. Sci. USA., 91, 1927–1931), and 12 human SOX genes have been identified (Denny et al., 1992, Nucleic Acids Res., above; Farr et al., 1993, Mammal. Genome, 4, 577–584; Gozé et al., 1993, Nucleic Acids Res., 21, 2943; Stevanovic et al., 1993, Human Mol. Genet., 3, 2013–2018).

Articles by Sinclair et al. (1990, Nature, 346, 240–244), Koopman et al. (1991, Nature, 351, 117–121) and Goodfellow & Lovell-Badge (1993, Ann. Rev. Genet., 27, 71–92) referred to hereinafter also confirm that SRY is a dominant inducer of testis development in mammals. Since the discovery of SRY, many other genes have been identified that encode related HMG boxes.

The identification and cloning of SRY depended on the investigation of the genomes of patients with sex reversal syndromes, some with chromosomal rearrangements. In addition to SRY on the human Y chromosome, at least five autosomal and one X-lined loci have also been linked with XY female sex reversal and the failure to develop a testis (Bernstein, R. et al., 1980, J. Med. Genet., 17, 291–300; Pelletier, J. et al., 1991, Nature, 353, 431–434; Bennett, C. P. et al., 1993, J. Med. Genet, 30, 518–520; Wilkie, A. O. M. et al., 1993, Am. J. Med. Genet, 46, 597–600; Bardoni, B. et al., 1994, Nat. Genet, 7, 497–501; Luo, X. et al., 1994, Cell, 77, 481–490). Four of these loci have been defined by the study of rare chromosomal rearrangements. Duplications of the X chromosome short arm cause XY female development (Bernstein, R. et al, 1980, supra). The sex reversal in these patients results from the presence of two active copies of DSS (dosage sensitive sex reversal gene) which maps to a 160 kb region of Xp21 (Bardoni, B. et al., 1994, supra). Autosomal loci on chromosome 9p and on 10q have been implicated by chromnosomal deletions in XY females (Bennett, C. P. et al., 1993, supra; Wikie, A. O. M. et al., 1993, supra). It is not known if the sex reversal in these instances is due to monosomy for dosage sensitive genes or whether the deletions reveal recessive mutations. A third autosomal locus, SRA1, is on chromosome 17 (Tommerup, N. et al., 1993, supra) and, in this case, the sex reversal is associated with CD. The diagnosis of CD is not entirely straightforward. The most conspicuous feature is congenital bowing and angulation of the long bones. However, this type of bowing is also seen in other skeletal dysplasias (McKusick, V. A., 1992, Mendelian Inheritance in Man., The Johns Hopkins Press, Baltimore). Other features may include a variety of skeletal deformities associated with bone and cartilage formation. Patients usually die in the first week of life from respiratory failure, however, the severity of the phenotype is variable and a few patients are mildly affected and survive into adult life. A striking feature of CD is the associated sex reversal. To date there have been at least 121 reported cases of CD. Of those that have been karyotyped, 24 are 46,XX females, 14 are 46,XY males. 34 are 46,XY females (with a gradation of genital defects) and two are cases of ambiguous genitalia with an XY karyotype (Tommerup, N. et al., 1993, supra; Young, I. D. et al., 1992, J. Med. Genet, 29, 251–252; Houston, C. S., et al., 1983, supra). The remaining 47 non-karyotyped cases show a skewed sex ratio of 31:16 in favour of females. Some of the sex reversed cases examined histologically exhibit gonadal dysgenesis implying that the gene(s) responsible for CD also plays a part in testis formation.

The inheritance pattern of CD is not obvious. Many reviewers have concluded that autosomal recessive inheritance is the most likely (Cremin, B. J., et al., 1973, Lancet, 1, 488–489), although it is difficult to distinguish this pattern from autosomal dominant inheritance with variable penetrance. Similarly, it is not clear if the bone malformation and sex reversal are caused by mutation of a single gene or of a pair of linked genes in a contiguous gene syndrome. Five chromosomal rearrangements associated with CD and sex reversal have been reported which localise the gene(s) responsible to the long arm of human chromosome 17 (Tommerup, N. et al., 1993, supra; Young, I. D. et al., 1992, supra; Maraia, R. et al., 1991, Clin. Genet, 39, 401–408). Recently, Tommerup et al., 1993, supra have refined this localisation to 17q24.1-25.T with GH and TK as flanking markers. A high resolution nap has been constructed across this 20 Mb region using a panel of whole genome radiation hybrids. The map has been used to position the translocation breakpoint from a 46,XY,t(2;17)(q35;q23–24) sex reversed campomelic dysplasia individual (Patient E) (Young, I. D. et al., 1992, supra).

SUMMARY OF THE INVENTION

It has now been found that DNA sequences of the Sox-9 and SOX-9 genes have now been elucidated and thus preparation of recombinant proteins encoded by these genes can be facilitated. An isolated DNA molecule combining these sequences and/or the recombinant proteins can be utilised therapeutically in relation to regeneration of bone or cartilage as described hereinafter.

Therefore, in one aspect, the invention provides an isolated DNA molecule comprising a DNA sequence selected from a group consisting of:

(i) a sequence of nucleotides as shown in FIG. 1 (SEQ ID NO:18);

(ii) a sequence complementary to the sequence according to (i); and (iii) a sequence having up to 21% variation from the sequences according to (i) or (ii) which sequence is capable of hybridising thereto under standard hybridisation conditions which codes for a polypeptide of the SOX-9 type.

In another aspect, the invention provides an isolated DNA molecule comprising a DNA sequence selected from a group consisting of:

(a) a sequence of nucleotides as shown in FIG. 8a (SEQ ID NO:20);

(b) a sequence complementary to the sequence according to (a); and (c) a sequence having up to 18% variation from the sequences according to (a) or (b) which sequence is capable of hybridising thereto under standard hybridisation conditions and which code for a polypeptide of the SOX-9 type.

The Invention also provides recombinant proteins encoded by both the Sox-9 gene and the SOX-9 gene as described hereinafter.

The Sox-9 sequence (iii) discussed above and the SOX-9 sequence (c) discussed above correspond to hybrids of the DNA sequences shown in FIGS. 1 and 8a (SEQ ID NOS:18 and 20) as such hybrids may be isolated by standard hybridisation methods as described in Sambrook et al. (1989, in Molecular Cloning: A Laboratory Manual Cold Spring Harbour Laboratory Press, New York; in particular sections 9.31 to 9.59), or direct sequence comparison.

Hybrids of the above mentioned sequences may be prepared by a procedure including the steps of:

(i) designing primers which are preferably degenerate which span at least a fragment of the relevant DNA sequences referred to above; and (ii) using such primers to amplify said at least a fragment either from an original cDNA library or cDNA reverse transcribed from either poly $A^+$ RNA or total RNA which RNA is derived from an appropriate source referred to herein.

The recombinant protein may be prepared by a procedure including the steps of:

(a) ligating a DNA sequence encoding a recombinant protein of the SOX-9 type or biological fragment thereof into a suitable expression vector to form an expression construct;

(b) transfecting the expression construct into a suitable host cell;

(c) expressing the recombinant protein; and (d) isolating the recombinant protein.

The vector may be a prokaryotic or a eukaryotic expression vector.

Suitably, the vector is a prokaryotic expression vector.

Preferably, the vector is pTrcHisA.

The host cell for expression of the recombinant protein can be a prokaryote or eukaryote.

Suitably, the host cell is a prokaryote.

Preferably, the prokaryote is a bacterium.

Suitably, the bacterium is *Escherichia coli*.

Alternatively, the host cell may be a yeast or a baculovirus.

The recombinant protein may be conveniently prepared by a person skilled in the art using standard protocols as for example described in Sambrook et al., (1989, supra, in particular Sections 16 and 17).

In yet another aspect, the invention provides a method of regeneration of bone or cartilage by administration of a DNA molecule or protein referred to above to a subject suffering from bone or cartilage deficiency.

Preferably the DNA molecule or protein may be injected directly into joint tissue such as knees, knuckles, elbows or ligaments. Therefore, the compounds of the invention may be utilised as a therapeutic agent in regard to treatment of cartilage or bone damage caused by disease or aging or by physical stress such as occurs through injury or repetitive strain, e.g. "tennis elbow" and similar complaints. The therapeutic agent of the invention may also be utilised as part of a suitable drug delivery system to a particular tissue that may be targeted.

Other therapeutic applications for the compounds of the invention may include the following:

1. Use in cartilage and/or bone renewal, regeneration or repair so as to ameliorate conditions of cartilage and/or bone breakage, degeneration, depletion or damage such as might be caused by aging, genetic or infectious disease, wear and tear, physical stress (for example, in athletes or manual labourers), accident or any other cause, in humans, livestock, domestic animals or any other animal species;

2. Stimulation of skeletal development in livestock, domestic animals or any other animal species in order to achieve increased growth for commercial or any other purpose;

3. Treatment of neoplasia or hyperplasia of bone or cartilage, in humans, livestock, domestic animals or any other animal species;

4. Suppression of growth of skeletal components in livestock, domestic animals or any other animal species in order to achieve decreased growth for commercial or any other purposes; and 5. Alteration of the quality or quantity of cartilage and/or bone for any other purpose in any animal species including humans.

In a broader sense, the potential uses for the Sox-9 or SOX-9 gene or its protein product fall into two broad categories, viz. (1) the promotion of bone and/or cartilage differentiation and/or growth, and (2) the suppression of bone and/or cartilage differentiation and/or growth. As such the gene or its protein product (or any part or combination of parts of either), can be described as a therapeutic agent. Thus, the therapeutic agent may be Sox-9 or SOX-9 DNA or DNA fragments alone or in combination with any other molecule, Sox-9 or SOX-9 protein or protein fragments alone or in combination with any other molecule, antibodies to Sox-9 or SOX-9 alone or in combination with any other molecule, sense or anti-sense oligonucleotides corresponding to the sequence of Sox-9 or SOX-9 (alone or in combination with any other molecule). The method of administration of the therapeutic agent will differ depending on the intended use and on the species being treated (see Mulligan, 1993, Science, 260, 926–932; Morgan et al., 1993, Ann. Rev. Biochem., 62, 191–217). Such methods may include:

(i) Local application of the therapeutic agent by injection (Wolff et al., 1990, Science, 247, 1465–1468), surgical implantation, instillation or any other means. This method may be useful where effects are to be restricted to specific bones, cartilages or regions of bone or cartilage. This method may also be used in combination with local application by injection, surgical implantation, instillation or any other means, of cells responsive to the therapeutic agent so as to increase the effectiveness of that treatment. This method may also be used in combination with local application by injection, surgical implantation, instillation or any other means, of another factor or factors required for the activity of the therapeutic agent.

(ii) General systematic delivery by injection of DNA, oligonucleotides (Calabretta et al., 1993, Cancer Treat. Rev., 19, 169–179), RNA or protein, alone or in combination with liposomes (Zhu et al., 1993, Science, 261, 209–212), viral capsids or nanoparticles (Bertling et al., 1991, Biotech. Appl. Biochem., 13, 390–405) or any other mediator of delivery. This method may be advantageous for all intended uses (1–5 above) whether or not the effect is intended to be targeted to specific tissues or parts of the body, and regardless of whether the intended result is the stimulation or inhibition or suppression of Sox-9 or SOX-9 gene or protein activity. Where specific targeting is required, this might be achieved by linking the agent to a targeting molecule (the so-called "magic bullet" approach employing for example, an antibody), or by local application by injection, surgical implantation or any other means, of another factor or factors required for the activity of the therapeutic agent, or of cells responsive to the therapeutic agent.

(iii) Injection or implantation or delivery by any means, of cells that have been modified ex vivo by transfection (for example, in the presence of calcium phosphate: Chen et al., 1987, Mol. Cell Biochem., 7, 2745–2752, or of cationic lipids and polyamines: Rose et al., 1991, BioTech., 10, 520–525), infection, injection, electroporation (Shigekawa et al., 1988, BioTech., 6, 742–751) or any other way so as to increase the expression or activity of Sox-9 or SOX-9 (gene or protein) in those cells. The modification may be mediated by plasmid, bacteriophage, cosmid, viral (such as adenoviral or retroviral; Mulligan, 1993, Science, 260, 926–932; Miller, 1992, Nature, 357, 455–460; Salmons et al., 1993, Hum. Gen Ther., 4, 129–141) or other vectors, or other agents of modification such as liposomes (Zhu et al., 1993, Science, 261, 209–212), viral capsids or nanoparticles (Bertling et al., 1991, Biotech. Appl. Biochem., 13, 390–405), or any other mediator of modification. The use of cells as a delivery vehicle for genes or gene products has been described by Barr et al., 1991, Science, 254, 1507–1512 and by Dhawan et al., 1991, Science, 254, 1509–1512. Treated cells may be delivered in combination with any nutrient growth factor, matrix or other agent that will promote their survival in the treated subject.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 1(a)–1(d)

Figure 2:
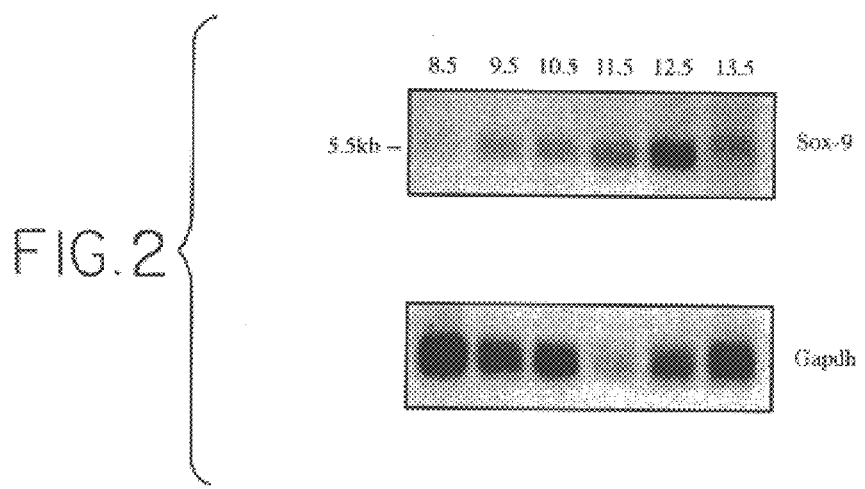

Nucleotide and predicted amino acid sequence of the mouse Sox-9 cDNA. The 2249 base-pair sequence (SEQ ID NO:18) reveals an open reading frame that potentially encodes a protein of 507 amino acids (SEQ ID NO:19) from the first methionine codon. There are five methionine codons (indicated in italics) upstream of the HMG box (boxed), but only the fourth of these is associated with a strong consensus sequence for initiation of translation (Kozak, 1989, J. Cell Biol., 108, 229). These five methionine codons are all conserved in the human Sox-9 homologue (SOX-9) sequence where they are also preceded by an in-frame stop codon (Foster et al., in press) A glutamine- and proline-rich region extends from amino acid position 339 to 507. There are multiple stop codons (not marked) following the end of the coding sequence and a putative poly-adenylation signal is indicated in lower case lettering. The positions of introns are indicated by arrows; these were determined by comparison of cDNA and genomic DNA sequences.

Methods: λgt10 10 dpc (Clontech) and λSHlox 11.5 dpc (Invitrogen) mouse embryo cDNA libraries and a λFIX II mouse 129SV genomic library (Gubbay et al., 1990, Nature, 346, 245–250), were screened for Sox-9 clones using a Sox-9 HMG box (Wright et al., 1993, Nucleic Acids Research, 21, 744) and subsequently non-box probes under highly stringent conditions. Sequence of cDNA clones were obtained from both strands in nested deletions. Sequencing was performed using a USB Sequenase kit and results were confirmed using a PRISM Ready Reaction DyeDeoxy Terminator Cycle Sequencing Kit and an Applied Biosystems DNA Sequencing System.

FIG. 2

Northern blot analysis of Sox-9 expression in mouse embryos. Poly(A)$^+$ RNA isolated from whole embryos at 8.5, 9.5, 10.5, 11.5, 12.5 and 13.5 dpc was hybridised with a Sox-9-specific probe (upper panel) and a probe for glyceraldehyde 3-phosphate dehydrogenase (Gapdh: lower panel).

Methods: Poly (A)$^+$ RNA was prepared from whole embryos using a Pharmacia QuickPrep mRNA Purification kit. Northern analysis (Sambrook et al., 1989, J. Molecular Cloning: A Laboratory Manual, 2nd Edition, Cold Spring Harbor Press, Cold Spring Harbor) was carried out using approximately 0.5 μg of each mRNA sample per lane. Following autoradiography, membranes were stripped of Sox-9 probe and re-hybridised with a $^{32}$P-labelled Gapdh probe to indicate the relative levels of mRNA in each lane. Transcript size was assessed by comparison to GIBCO-BRL 0.24–9.5 kb RNA ladder.

FIGS. 3a–3i

Wholemount in situ hybridisations and alcian blue cartilage staining showing expression of Sox-9 and cartilage matrix deposition in developing embryos:

a. 9.5 dpc whole embryo showing Sox-9 expression in the first bronchial arch (b1), rostral somites (so), otocyst (oc) and some surface ectodermal cells overlying the spinal cord (se);

b. Partial view of a 10 dpc embryo showing expression within the caudal somites (so) and ventricular cells of the forebrain (vc);

c. 10.5 dpc whole embryo showing initiation of expression in the limb buds (lb) and in the second bronchial arch (b2);

d. 10.5 dpc embryo stained with alcian blue dye. No cartilage is present at this stage, confirming that cartilage formation is preceded by Sox-9 expression;

e. 11.5 dpc showing advancement of expression in the limb buds, and onset in the scapula (s) and pelvis (p);

f. 12.5 dpc embryo showing staining in most skeletal structures;

g. alcian blue-stained 12.5 dpc embryo showing the cartilagenous skeleton at this stage; the otocyst, digits (d) and ribs (r) are indicated;

h. dorsal view of a 12.5 dpc embryo illustrating expression in ventricular cells of the spinal cord (vc); the otocysts are also indicated;

i. partial view of a 13.5 dpc embryo demonstrating that expression has progressed to the tips of the digits and the tail tip (t) where the cartilage is still being actively laid down but is switched off in more mature cartilage; staining is also seen in the vibrissae (v) at this stage.

Methods: Wholemount in situ hybridisations, using anti-sense and sense (not shown) RNA probes prepared from sub-clones of Sox-9 gene sequence 3' to the HMG box but not containing any HMG box or poly-A-tall sequences, were carried out according to Wilkinson et al., 1993, Methods Enzymol., 225, 361–373. Cartilagenous tissue in whole 10.5 and 12.5 dpc embryos was stained according to a protocol modified from Ojeda et al., 1970, Stain. Technol., 45, 137–138. Stained specimens were photographed on an Olympus stereomicroscope using Kodak Ektachrome film.

FIG. 4

Wholemount in situ hybridisation of chondrocytes in sections of mouse bone eight days post experimental fracture using anti-sense RNA probes (not shown) prepared from sub-clones of mouse Sox-9 gene sequences.

FIG. 5

Mapping of Sox-9. The approximate position of Sox-9 with respect to the markers D11Mit10 and D11Mit36, as indicated by a combination of interspecific backcross linkage date and haplotype analysis, is shown by bars A and B on the consensus linkage map of mouse chromnosome 11 (Buchberg et al., 1993, Mammal. Genome., 4, S164–S175), A; Sox-9 position relative to D11Mit10 and B; relative to D11Mit36. The relative locations of Sox-9 and Tail-short (Ts) cannot represented accurately as they were mapped relative to different markers in separate backcrosses. The locations of the neurological mutations Jackson shaker (js), teetering (tn) and cerebellar outflow degeneration (Cod) are also indicated. Genetic distance from the centromere is indicated in centiMorgans.

Methods: A gene-specific, single-copy cDNA probe was isolated from the region of Sox-9 3' to the HMG box and this probe was used to identify a restriction fragment length variant between the two mouse species *Mus spretus* and *Mus musculus* domesticus using the enzyme Pvuli (data not shown). Mapping was carried out by analysing the segregation of these variants relative to known markers in a subset of interspecific backcross progeny mice (The European Backcross Collaborative Group, 1994, Human Mol. Genet., 3, 621–627).

FIG. 6

Radiation hybrid map of 17q across the translocalion breakpoint in patient E. STS markers are written vertically above a solid bar representing genomic DNA. The markers flanking the translocation breakpoint are indicated. Below, flanking STS markers D17S970 and SOX-9 tested on the B1 hybrid by PCR showing their absence/presence respectively. B1 is an L-M Tk⁻ somatic cell hybrid containing the translocation chromosome 2pter-q35:17q23-qter from patient E; PCTBA1.8 is a mouse somatic cell hybrid containing human chromosomne 17 only; HFL is a human fibroblast; L-M TK⁻ is a mouse fibroblast.

Methods: The whole genome irradiation and fusion hybrids (WG-RH) were constructed by fusing A23 hamster fibroblasts with irradiated (6000 rads) HFL human fibroblasts (Walter, M. A. et al., 1994, supra). The STS order was determined using the RHMAP programmes (Boehnke, M. et al., 1991, Am. J. Hum. Genet, 49, 1174–1188). PCR reactions were performed with 50 ng of genomic DNA, 1.5 mM $MgCl_2$ (2.5 mM $MgCl_2$ for SOX-9 primers), 50 mM Kcl, 0.1% Triton-X100, 10 mM Tris-Cl (pH 8.5), 1.5 U Taq polymerase and 1 $\mu$M each primer. Thermocycling parameters were 94° C. for 30 seconds; 55° C. for 30 seconds; 72° C. for 60 seconds, then 5 mins at 72° C. The presence or absence of each STS in each WG-RH was determined by electrophoresis through ethidium bromide stained agarose gels. Primer sequences, AFMa346xg5-A, 5'CCAAAGTCCTAAAGGTGGG3'(SEQ ID NO:2); AFMa346xg5-B, 5'TTTCAGGCAAATAAGGCAG3'(SEQ ID NO:3); AFM189yb8-A, 5'TGGCAATCTAACAGATGAGA3'(SEQ ID NO:4); AFM189yb8-B, 5'TCNCAAATGTCATATATCCA3'(SEQ ID NO:5); SOX9-A, 5'AGTCCAGATTGACTGGAACACA (SEQ ID NO:6); SOX9-B, 5'GCAATAAGATACTAATATGTAGAG3'(SEQ ID NO:7) D17S40-A, 5'GTCAGCAGAAATCCTAAAGG3'(SEQ ID NO:8); D17S40-B, 5'GACTAATGCCGATGGTTAAG3' (SEQ ID NO:9). The other primer sequences are available through the genome data base (GDB).

FIG. 7

Relationship between the chromosome 17 radiation hybrid map, YAC contig and cosmid contig for the region of the Patient E translocation breakpoint. Markers are indicated vertically above a solid bar representing genomic DNA. YACs are positioned below: solid bars indicate confirmed marker content, dashed lines represent the possible extent of the YAC. Sizes indicated are for the entire YAC and may include non-chromosome 17 sequences present due to chimerism. The cosmid walk is shown below an expansion of the breakpoint region genomic DNA. The organisation and orientation of SOX-9 are indicated. ICRF Reference Library YAC and cosmids (Lehrach, H. et al., 1990, supra) are indicated as such, all other YACs are from Centre d'Etude du Polymorphisme Humain (Cohen, D. et al., 1993, supra).

Methods: YAC and cosmid ends were isolated by vectorette PCR (Riley, J. et al., 1990, Nucleic Acids Res., 18, 2887–2890) using the published YAC primers and cosmid vector (Lawrist4) primers LAW4L: CGCCTCGAGGTG-GCTTATCG (SEQ ID NO:10) and LAW4R: ATCATACA-CATACGATTTAGGTGAC (SEQ ID NO:11).

Figure 8B:
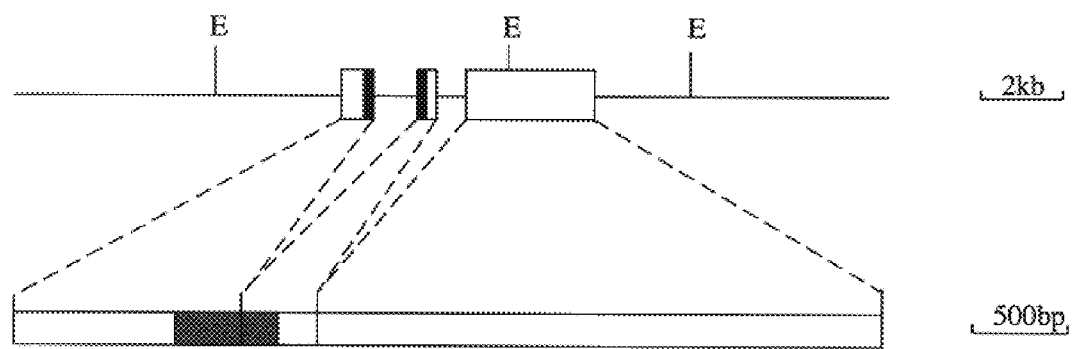

FIGS. 8a(i)–8a(iv)

Nucleotide and predicted amino acid sequence of SOX-9(SEQ ID NOS:20≧21). Numberings is with respect to the A in the first methionine codon of the open reading frame. An in-frame 5' stop codon and the predicted termination stop codon are in bold. The HMG box is boxed and the proline- and glutamine-rich region is underlined. The locations of the introns are indicated with arrows and a potential polyadenylation signal is indicated by bold, italic letters.

FIG. 8b

Genomic organisation of the SOX-9 gene. The solid bar represents genomic DNA. The SOX-9 exons are boxed and the HMG box cross hatched. The positions of the introns are indicated.

Methods: Initial cDNA clones were obtained by screening a lambda gt 10 human testis library (Clontech) using a SOX-A box probe (Stevanovic, M, et al., 1993, supra). A composite transcript was determined from these overlapping clones and from further clones obtained from an HT1080 (fibrosarcomel cDNA library (a kind gift of D. L. Simmons) and a human foetal brain library (HGMP Resource Centre, Harrow). Sequencing was performed using the dideoxy chain termination method. The location of the intron/exon boundaries was determined by restriction mapping of genomic and cDNA clones and by comparison of the genomic and cDNA sequences. Initial localisation of the SOX-9 cDNA to chromosome 17 was determined by probing a somatic cell hybrid panel. Sublocalisation to 17q23-qter was determined using a panel of chromosome 17 deletion hybrids including PCTBA1.8, TRID62, PLT8, PJT2A1 and DCR1 (Black, D. M. et al., 1993, E. Am. J. Hum. Genet., 52, 702–710) and refined to 17q24 by fluorescence in situ hybridisation to normal human metaphase spreads.

FIG. 9

Figure 10A:
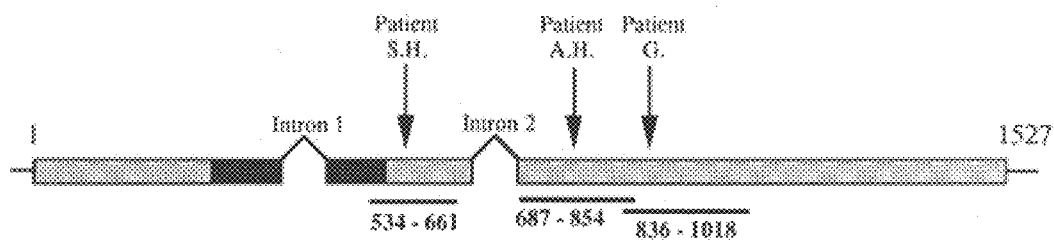
Figure 10B:
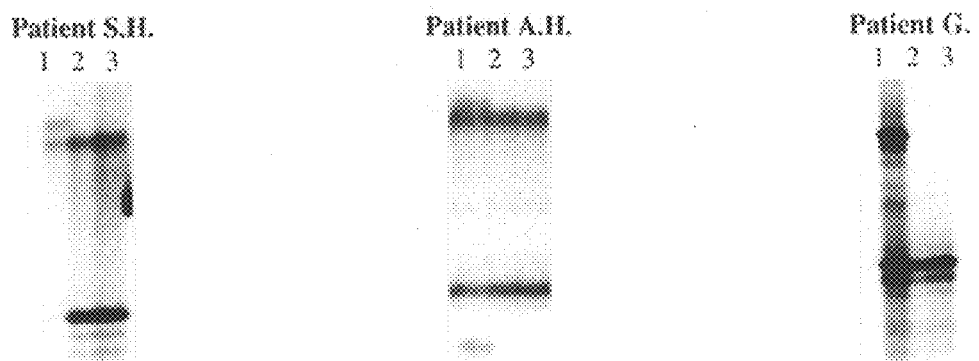
Figure 10C:
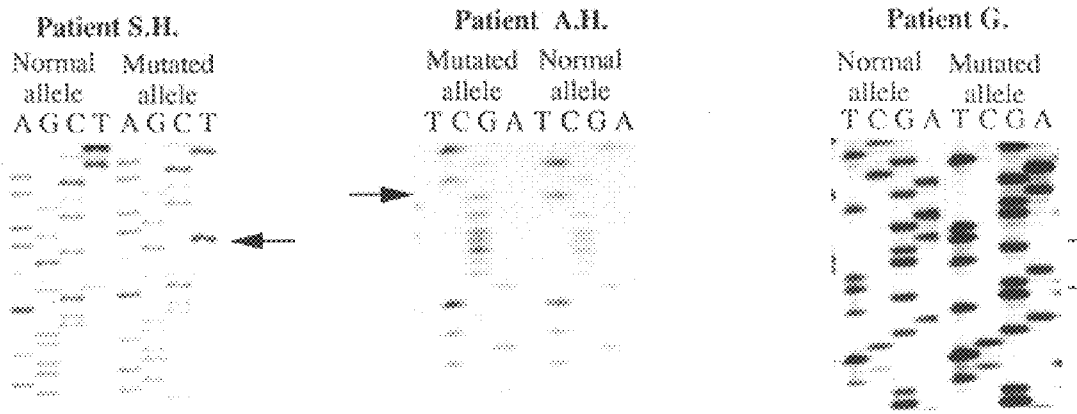

Diagrammatic representation of mouse Sox-9 gene structure. Numerals above the line denote the nucleotide position of the mouse Sox-9 gene having regard to the DNA sequence shown in FIG. 1. The gene comprises a 5' untranslated region (nts 1-301), region A (nts 302–607), a HMG box (nt 608–843), region B (nts 844–1321), P/Q/A—rich region (nts 1322–1429), region C (nts 1430–1822) and the 3' untranslated region (nts 1823–2249), FIGS. 10a–10c Single-strand conformation polymorphism (SSCP) and sequence analysis of SOX-9 in campomelic dysplasia patients.

FIG. 10a

SOX-9 open reading frame (shaded boxes) showing the HMG box (heavy shadring). Numbers indicate nucleotide sequence beginning with the A of the first methionine, with introns occurring after nucleotides 431 and 685. Solid bars below indicate regions of the ORF generating unique SSCP conformers. Positions of mutations are indicated by arrows.

FIG. 10b

SSCP using primers indicated in (a). Lane 1; patient DNA. For Patients S.H. and G., lanes 2 and 3 are DNAs from father and mother, respectively. For Patient A. H., lanes 2 and 3 are DNAs from unrelated (normal) individuals.

FIG. 10c

Sequencing gels of normal and mutated patient alleles. The position of each mutation is indicated. Sequence for Patients S.H. and A.H. is the coding strand; Patient G. sequence is the non-coding strand.

Methods: Primer sequences: 534, 5'GAGGAAGTCGGTGAAGAAC3'(SEQ ID NO:12); 661, 5'TCGCTCATGCCGGAGGAGGAG3'(SEQ ID NO:13); 687, 5'GCAATCCCAGGGCCCACCGAC3'(SEQ ID NO:14); 854, 5'TTGGAGATGACGTCGACTGCTC3'(SEQ ID NO:15); 836, 5'GCAGCGACGTCATCTCCAAC3'(SEQ ID NO:16); 1018,5'GCTGCTTGGACATCCACACGT3' (SEQ ID NO:17). PCRs (10 $\mu$l) were performed as in FIG. 1 with the non-radioactive dCTP concentration reduced to 1/10 and the addition of 0.05 $\mu$l of [$\alpha$-$^{33}$P]dCTP (1000–3000 Ci mmol$^{-1}$, 10 mCi ml$^{-1}$) and 0.2 $\mu$M of each primer. Reactions were cycled for 30 sec at 94° C., 30 sec at 65° C. (534–681 and 836–1018) or 70° C. (687–854), 45 sec at 72° C. for 35 cycles. PCR products were denatured by adding 10 $\mu$l of 0.2% SDS, 20 mM EDTA then 10 $\mu$l 95% formamide, 20 mM EDTA, 0.05% bromophenol blue, 0.05% xylene cyanol and heating to 100° C. for 5 min. Two $\mu$l were loaded onto 6% acrylamide:Bis-acrylamide (37.5:1), 5% glycerol gels. Electrophoresis was carried out at 25 W at 40° C. PCR products from duplicate reactions ware subcloned and at least 10 clones from each were sequenced by either the dideoxy chain termination method or by DyeDeoxy Terminator Cycle Sequencing (ABI). DNA profiling of each family using 12 chromosome 8 microsatellite markers (heterozygosity>70%) showed no discordant results between parents and offspring.

EXPERIMENTAL

Preliminary Discussion

It has now been discovered surprisingly that expression of Sox-9 is evident at sites where the primitive mesenchyme is condensing in the early stages of cartilage formation. It is therefore proposed that the Sox-9 gene product regulates the expression of other genes involved in chondrogenesis by acting as a transcription factor for these genes.

As will be demonstrated hereinafter, Sox-9 is predominantly expressed in mouse embryos in mesenchymal cells as they condense to form hyaline cartilage and is switched off once chondrogenesis is complete, consistent with a determinative role in skeletal formation. Expression and chromosomal mapping of Sox-9 suggest that it may be the gene defective in the skeletal mutant Tail-short.

During embryogenesis, genetic switches act to commit undifferentiated cells to their appropriate developmental pathways. Although the master regulatory genes that constitute these switches hold The key to our understanding of how embryonic development is controlled, only a few such genes have been identified in mammals. One example is the MyoD1 gene which alone is sufficient to activate expression of all the genes which are required to produce the muscle phenotype; introduction of MyoD1 cDNA into undifferentiated fibroblasts converts them into myoblasts (Davis, 1987, Cell 51 987–1000). Another developmental switch gone is the Y-linked testis-determining factor Sry referred to above. Sry is responsible for directing differentiation of cells in the different gonad to form a testis; subsequent male development is due to signals produced by the mature cells of the testis. Sry and MyoD1 are DNA binding proteins and MyoD1 has been shown to bind to a site in the promoters of other muscle-specific genes and subsequently activate their transcription (Piette, 1990, Nature, 345, 353–355; Lasser, 1989, Cell 58, 823–831. Sry is presumed to activate transcription of genes downstream in the sex-determination pathway, although these genes have not yet been identified.

During skeletogenesis, most bones are laid down initially as a framework of hyaline cartilage. In this process, mesenchyme condenses and assumes the approximate shape of the bone, chondroblasts differentiate within this structure and extracellular matrix proteins characteristic of this type of cartilage are synthesised. These cartilage models are subsequently transformed into bone as calcium salts are deposited within them during ossification.

Characterisation of the Mouse Sox-9 Gene

By screening mouse embryo cDNA libraries with a Sox-9 HMG box probe, three incomplete but overlapping clones were identified. The nucleotide and deduced amino acid sequences of a composite cDNA molecule are shown in FIG. 1. The 2249 base-pair sequence (SEQ ID NO:18) reveals an open reading frame that potentially encodes a protein of 507 amino acids from the first methionine codon (SEQ ID NO:19). There are three other AUG codons upstream of the HMG box but only the last of these (position 26, FIG. 1) is associated with a strong consensus sequence for initiation of translation (Kozak, 1989, J. Cell Biol., 108, 229). There are multiple stop codons (not shown) following the end of the coding sequence and a putative poly-adenylation signal AATTAAA (SEQ ID NO:1) is present 14 bases upstream of a poly-A tail. Comparison of Sox-9 PCR product sizes from cDNA and genomic DNA templates, and sequencing of Sox-9 geonomic clones revealed two introns, one of which interrupts the HMG box domain (FIG. 1). This is the first report of introns in any member of the Sox gene family in the mouse, although introns have also been identified in the same positions in human and chick Sox-9 homologues.

Sox-9 cDNA sequence 3' to the HMG box is rich in both glutamine and proline residues, a common feature amongst the activation domains of known RNA polymerase II transcription factors (van de Watering, 1991, EMBO J., 10, 123–132; Mermod, 1989, Cell, 58, 741–753; Courey, 1988, Cell, 55, 887–898; Clerc, 1988, Genes Dev., 2, 1570–1581; Scheidereit, 1988, Nature, 336, 551–557; Muller, 1988, Nature, 336, 544–551; Norman, 1988, Cell, 55, 989–1003). It has now been demonstrated that this domain of the Sox-9 protein can function as a transcriptional activator in vitro using the yeast GAL4 assay (Lillie, 1989, Nature 338 39–44). Transcription of the CAT reporter gene was activated following co-transfection with vectors which directed expression of GAL4/Sox-9 fusion proteins containing either the whole of the Sox-9 open reading frame, or the putative activation domain from amino acid positions 329 to 507 (data not shown).

Expression of Sox-9 During Mouse Embryogenesis

Sox-9 expression was examined in whole embryos by Northern blotting of polyA$^+$ RNA. The size of the mRNA was shown to be approximately 5.5 kb, indicating that there is a considerable region of 5' untranslated sequence which is not present in any of the cDNA clones. Expression of Sox-9 mRNA was detected from 8.5 dpc through to 13.5 dpc, peaking at 12.5 dpc (FIG. 2).

Figure 3A:
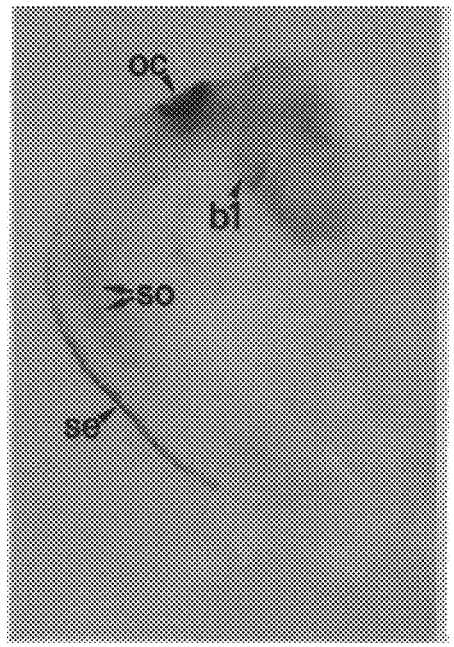
Figure 3B:
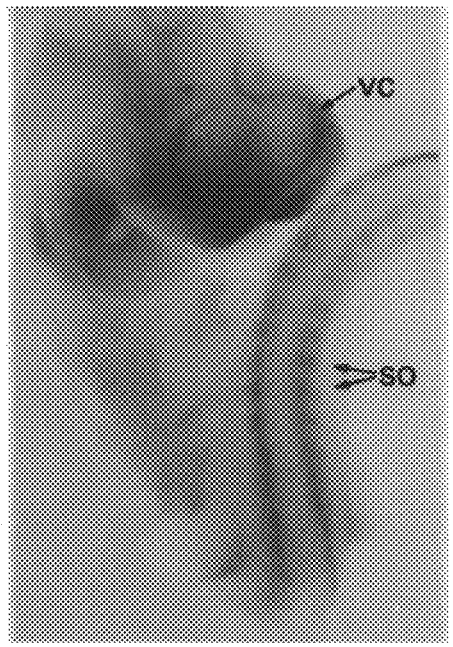

Wholemount in situ hybridisation showed Sox-9 expression in mesenchyme in the head and the first branchial arch, and also in the more mature rostral somites at 9 dpc (FIG. 3a). Strongest expression at this stage occurred in the otocysts and in a scattered population of surface ectoderm cells overlying the spinal cord for a distance of several somite lengths, located near the middle of the anteroposterior axis. The significance of this letter staining is not clear, but it persists at least until 13.5 dpc, moving gradually in a caudal direction as the axis extends. At 10 dpc, intense staining was present in the facial and first bronchial arch mesoderm (FIG. 3b) and expression had extended to all somites. However, in the less mature caudal somites, staining was seen in a discrete population of cells within each somite, consistent with expression in the sclerotome compartment which gives rise to the cartilage of the trunk; in the more mature rostral somites, evidence of sclerotomal migration could be seen. Intense staining persisted in the otocysts. Some signal was observed in tubular structures in the heart. Curiously, ventricular cells of the fore and midbrain were positive, but less mature regions of the central nervous system (including hindbrain and spinal cord) were negative. This staining of the ventricular cells moved further caudally in later stages, reaching the tail by 11.5 dpc (see FIG. 3h).

Figure 3C:
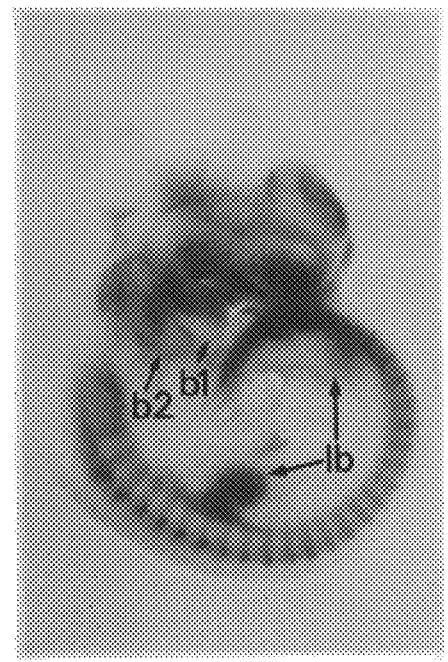
Figure 3D:
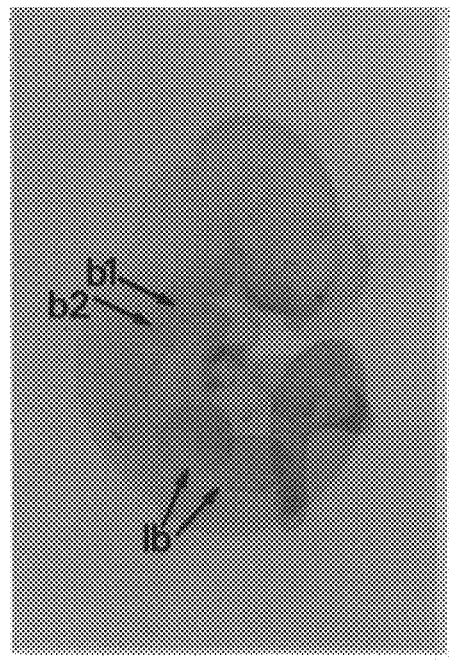

At 10.5 dpc, strong staining was seen in the mesoderm surrounding the nostril invaginations (FIG. 3c). Strongly staining condensations were present in the first and second branchial arches, and also in the limb buds. The limb bud condensations acquire strong Sox-9 expression in a very short time (no staining was observed at 10 dpc), and clearly precede the deposition of cartilage in these sites, as judged by alcian blue staining of embryos (FIG. 3d). This indicates that Sox-9 is likely to be the cause rather than the consequence of chondrocyte differentiation. In the forelimb buds, there were in fact two distinct but overlapping condensations, the more proximal of which was presumably the humeral condensation. At this stage, Sox-9-positive sclerotomal cells could clearly be seen migrating from the rostral somites (FIG. 3c), but remained within the confines of the caudal somites. Expression in the otocysts had decreased in the period 10 to 10.5 dpc, and continued to decrease subsequently. Staining was clearly visible in the notochord in the tail region posterior to the hindlimb bud; more anterior staining, if any, may have been obscured by the depth of the notochord within the embryo.

Figure 3E:
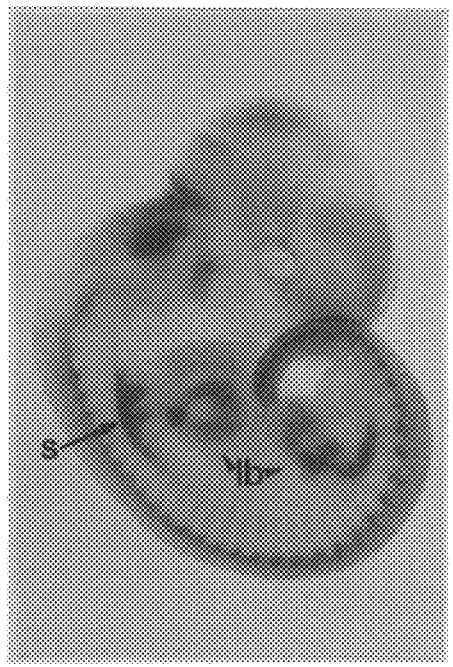
Figure 3F:
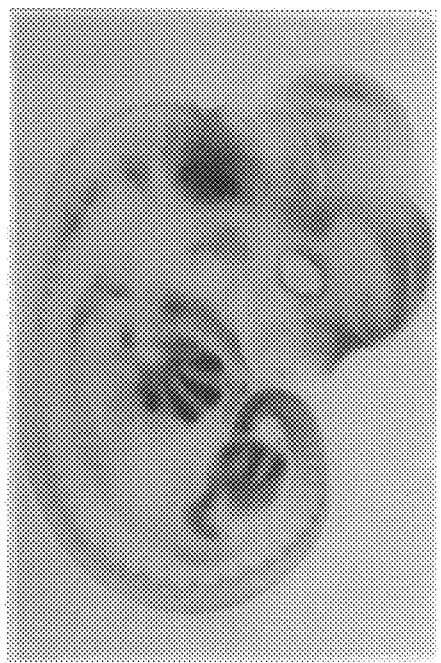

The pattern of Sox9 expression associated with the developing limbs became more complex in subsequent days. By 11.5 dpc, the more distal condensation had progressed to form radius, ulna and footplate condensations (FIG. 3e). In addition, a prominent girdle corresponding to the scapula was strongly positive for Sox-9.

Figure 3G:
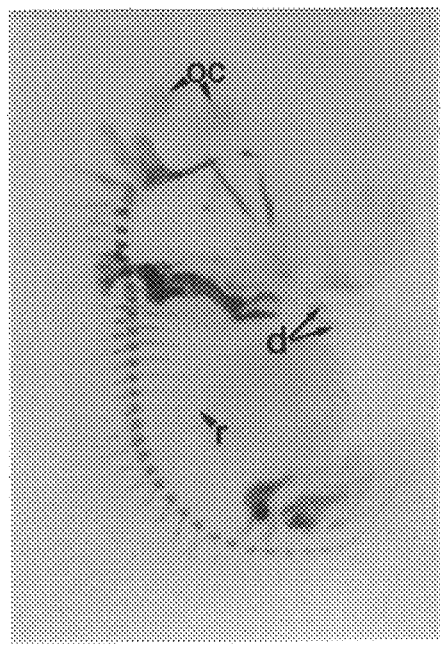
Figure 3H:
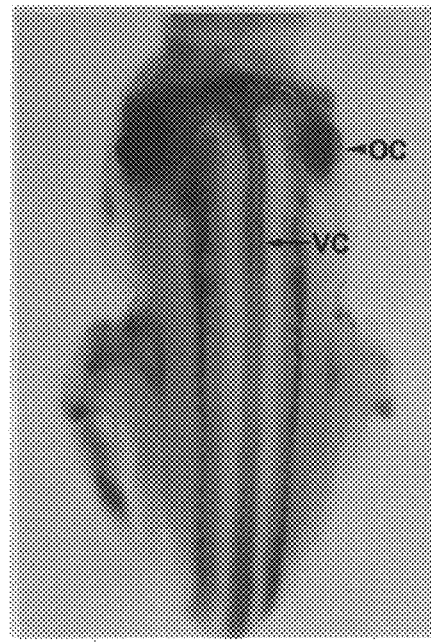

The correlation between Sox-9 expression and skeletal development was most striking at 12.5 dpc (FIG. 3f), when staining was observed in most skeletal structures visualised by alcian blue staining (FIG. 3g). Sox-9 expression was evident in the developing vertebrae, ribs, long bones, digits and cranial cartilage. At some sites, such as where the digits were forming at 12.5 dpc, the domain of Sox-9 expression was broader than that of the alcian blue staining, reinforcing the suggestion that Sox-9 is expressed not only in chondrocytes but also in their condensing mesenchymal progenitor cells. At this stage the expression in the ventricular cells of the spinal cord was clearly visible as two parallel stripes when viewed dorsally (FIG. 3h).

Figure 3I:
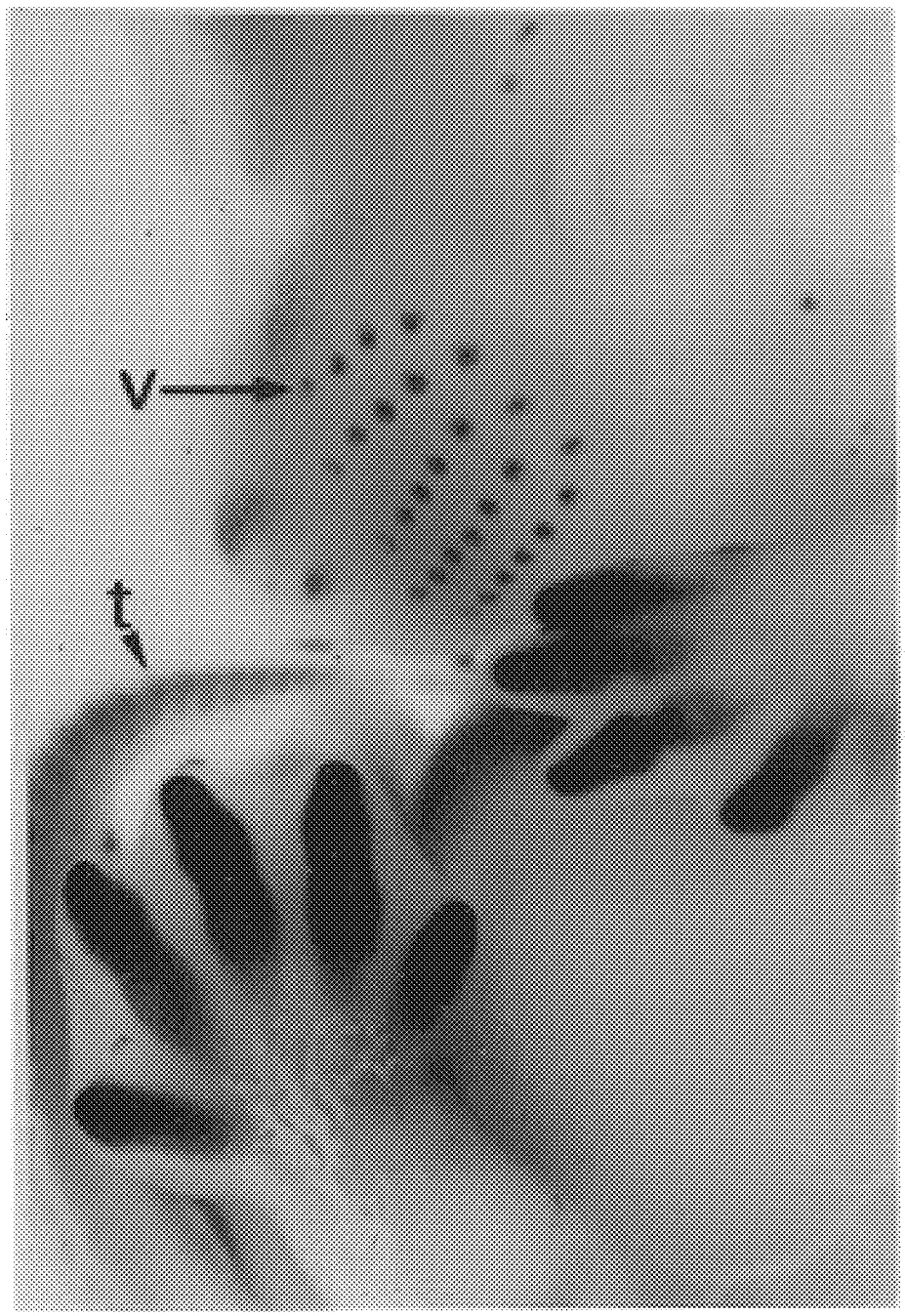

By 13.5 dpc, Sox-9 staining was confined to the tail-tip vertebrae, the tips of the digits, the ribs and the nasal cartilage, where chondrogenesis was still in progress, and was no longer seen where chondrogenesis was complete, for example, in the long bones of the limbs and the proximal parts of the digits (FIG. 3i). Prominent staining was also observed in the vibrissae. The staining of ventricular cells of the spinal cord was by this time only observed posterior to a point midway between the fore- and hindlimbs, apparently regressing in an anterior to posterior direction.

Experimental Bone Fracture Induces Expression of Sox-9

Figure 4:
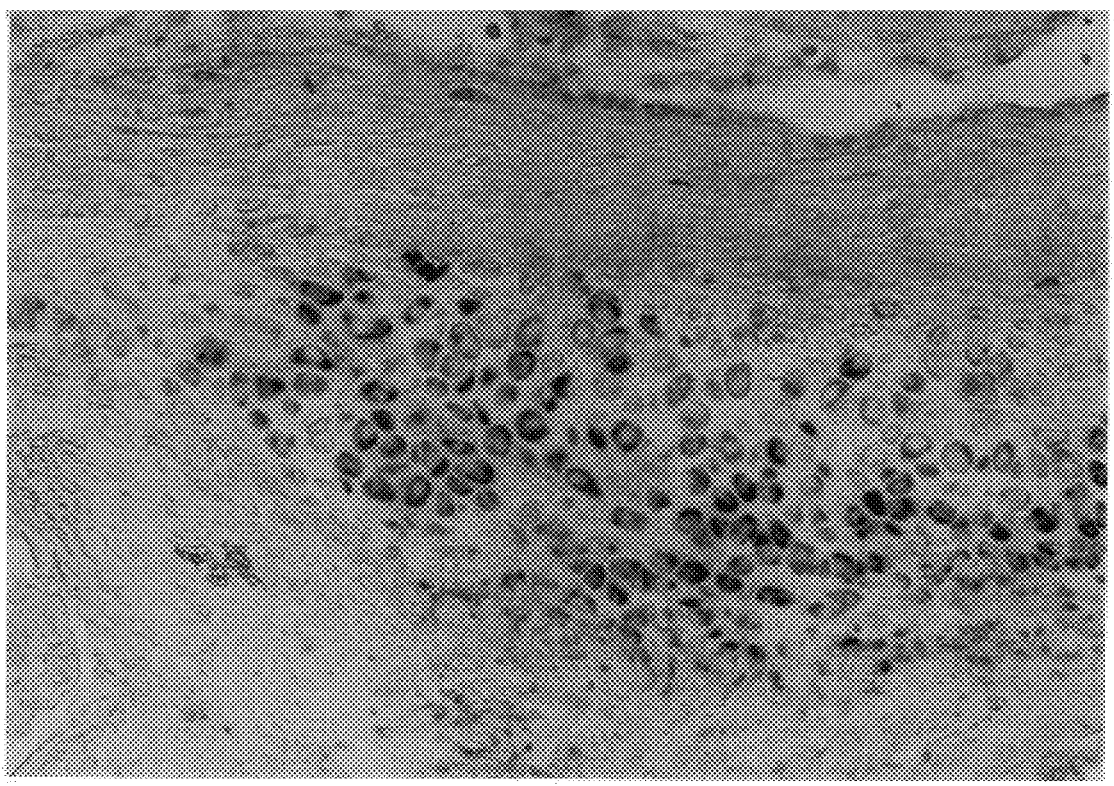

Wholemount in situ hybridisation studies using a Sox-9 antisense probe have revealed that subsequent to experimental fracture of mouse bone in accordance with the method described in (Nakase, et al., 1995, J. Bone and Min. Res., 9, 651–659), strong expression of Sox-9 was obtained in chondrocytes at eight days post-operation (FIG. 4) whereas there was no expression of Sox-9 detected in control chondrocytes (data not shown). These results indicate that Sox-9 gene expression is transiently induced by experimental bone fracture.

Linkage Analysis

Figure 5:
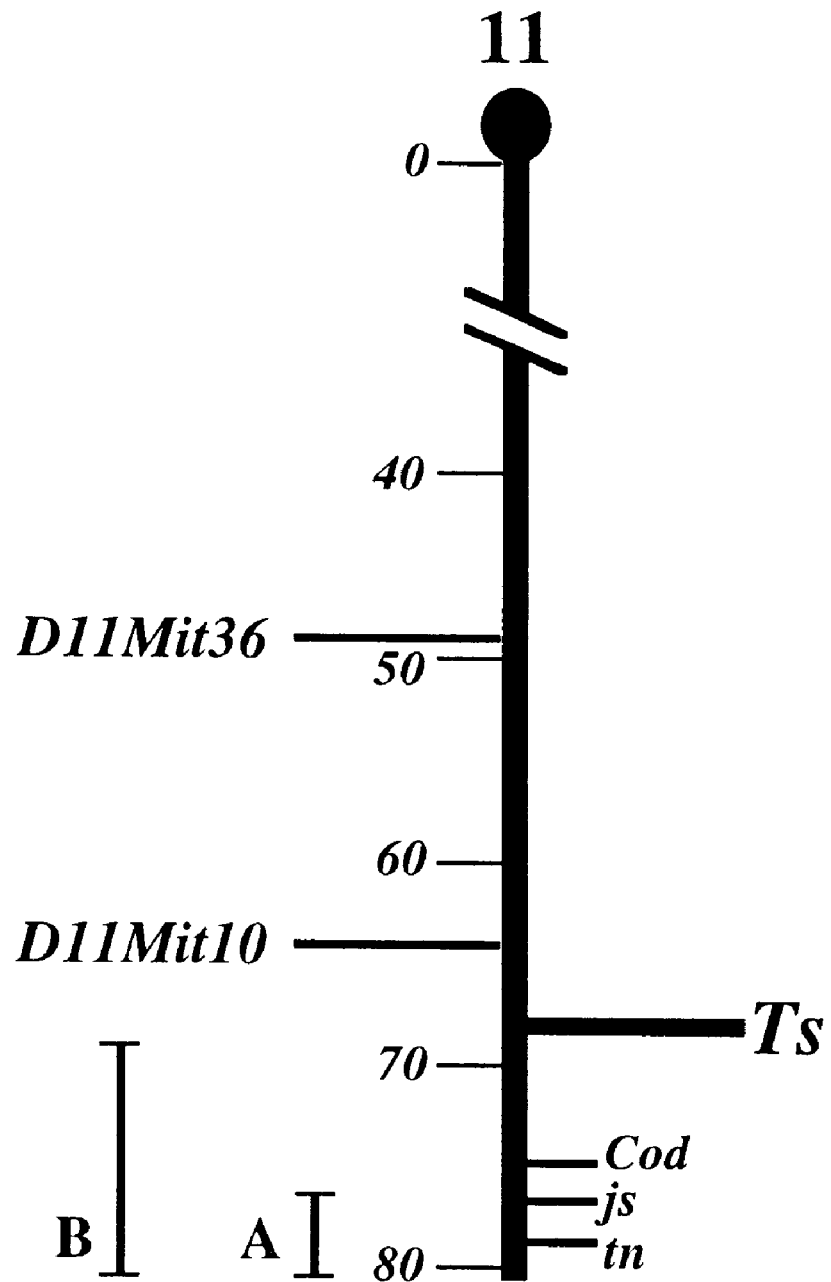

Using the interspecific backcross method, Sox-9 was mapped to distal chromosome 11. Linkage analysis suggested a localisation 18.0±5.4 cM from the marker D11Mit10, or 26.5±6.3 cM from the marker D11Mit36 (FIG. 5). Chromosome 11 haplotype analysis of recombinants from this backcross indicates that Sox-9 maps distal to D11Mit10. Known mouse developmental mutants that map to this region include the neurological mutants Jackson-shaker (js), teetering (tn) and cerebellar outflow degeneration (cod) (FIG. 5) (Buchberg, 1992, above). Amongst mutations in this region is Tail-short (Ts) referred to above. Homozygous Ts blastocysts are unviable but heterozygotes survive and are small with shortened, kinked tails caused by reduced number and dysmorphology of caudal vertebrae, and display a variety of skeletal abnormalities as described above. These include vertebral fusions and dyssymphyses, dysmorphology of the humerus, tibia, femur and radius, digital triphalangies and fusions, additional ribs and rib fusions and various abnormalities of the skull. The notochord, neural tube and heart are malformed. The skeletal abnormalities displayed by Ts mice all occur in tissues where Sox-9 is expressed during development. In view of the mapping and expression data, Sox-9 is a good candidate for the gene defective in Tail-short mice.

It has been demonstrated that Sox-9 is involved in the formation of the skeleton during mouse embryogenesis. It is strongly expressed at sites where skeletal components are being laid down as cartilage.

Our observations suggest that Sox-9 expression is a cause rather than a consequence of chondrocyte differentiation. First, Sox-9 expression precedes the deposition of cartilage in all skeletal elements. Sox-9 expression is the earliest known marker of sclerotomal cells, the primordial calls that give rise to trunk cartilage. In the digits Sox-9 is expressed in a broader domain than that where cartilage matrix had already been laid down, indicating that it is initially switched on in loosely packed progenitor cells and is expressed throughout the condensation process.

Secondly, expression of Sox-9 ceases soon after deposition of cartilage; by 13.5 dpc the staining in the long limb bones and proximal ends of the digits was no longer visible, but was maintained in sites where chondrogenesis persists, such as the tail and digit tips. The short period of Sox-9 expression suggests that Sox-9 has a role during initiation of chondrogenesis and is no longer required once condensation is complete and cartilage-spcific protein synthesis begins. The temporary expression of Sox-9 is similar to that of the closely related testis determining gene Sry, and suggest that Sox-9 may act as a genetic switch in determining the fate of the mesenchymal cells in which it is expressed.

Thirdly, it is likely that Sox-9 functions as a transcription factor, as do the products of several other members of the Sox gene family. Sox-9 contains an HMG box (a motif known to act as a site-specific DNA-binding domain) and we have demonstrated ability of its carboxyl terminus to activate transcription of a reporter gene. It therefore seems likely that Sox-9 activates genes downstream in the chondrogenic pathway. Such genes may include regulatory molecules such as members of the bone morphogenetic protein family (reviewed by Kingsley, 1994, Trends Genet., 10, 16–21) or structural genes such as α1 (II) collagen, which is a major component of cartilage.

The expression patterns of Sox-9 in the developing skeleton and in other tissues, such as the notochord, central nervous system and heart, correlate with defects that occur in Ts embryos. In addition, mouse Sox-9 maps to the Ts locus. Taken together, these data implicate Sox-9 in the genetic defect Tail-short (Ts). While our data provide a ready explanation for the skeletal defects in Ts mice, it is not clear how defects in Sox-9 might explain the anaemia exhibited by Ts embryos (Deol, 1961, above); we were unable to defect Sox-9 expression in the yolk sac where Ts mice have reduced blood islands at an early stage. The semi-dominant nature of this mutation may be due to haploinsufficiency, in which two functional copies of the gene are required to produce enough product for normal development. However, the inviability of Ts homozygote blastocysts implies that the gene responsible for the Ts defect must be aberrantly expressed at the blastocyst stage, and no expression of Sox-9 in blastocysts was detected at 4 dpc. It is possible that Sox-9 is expressed earlier than 4 dpc. Alternatively, the defects may be a result of overexpression or inappropriate expression directed by the mutant allele.

Expression of Sox-9 was observed in several non-skeletal tissues both during development and in the adult. In some tissues this may be a reflection of the presence of chondrocytes. In the brain and spinal cord, Sox-9 is clearly expressed in the rapidly dividing neurones of the ventricular zone. A common symptom of campomelic dysplasia is mental retardation, suggesting that the observed expression in the developing central nervous system, and possibly also in the adult brain, has a functional significance. We also observed expression of Sox-9 in mouse fetal genital ridges and early gonads. As XY sex reversal often associated the campomelic dysplasia (Hovmoller, 1977, supra), Sox-9, like its Y-linked relative Sry, must also have a role in sex determination, at least in humans. It is not yet known whether Sox-9 and Sry are expressed in the same cell type, nor whether Sox-9 interacts with, competes with, or acts downstream from Sry. Sex reversal has not been noted for Ts mice, and it is possible that the mutant allele involved in Ts does not cause the sex reversal phenotype. Gain- and loss-of-function analyses in transgenic mice will be necessary to elucidate the roles of Sox-9 in sex determination as well as in neural and skeletal development.

HUMAN SOX-9

Preliminary Discussion

Adjacent to the translocation breakpoint as hereinbefore described, a human SOX-9 has been found. Mutation analysis and sequencing of SOX-9 in clinically confirmed campomelic patients without cytologically detectable chromosomal arrangements have identified several mutations as described hereinafter. Detailed data are presented for three patients, two with confirmed de novo mutations, one of which occurs in an XY female, demonstrating that mutations in this gene cause both CD and SOX reversal.

Construction of a High Resolution Map of 17q24.1-q25.1

Figure 6:
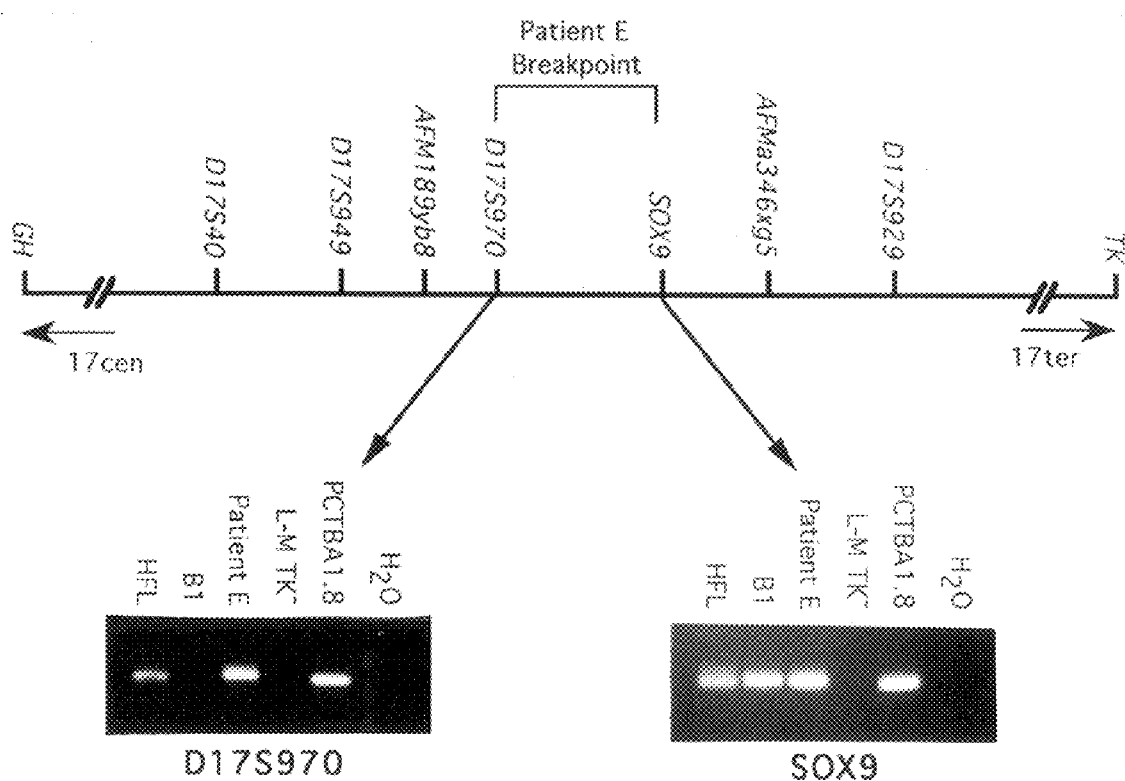

Radiation hybrid mapping allows the integration of different types of markers into a single map (Walter. M. A. et al., 1993, Trends in Genetics, 9, 352–356; Walter, M. A. et al., 1994, Nature Genet., 7, 22–28). We have used PCR to screen DNA samples from a panel of 129 whole genome radiation-fusion hybrids with a total of 38 STS markers across the region from GH to TK on chromosome 17. These markers include 26 microsatellites, 2 anonymous DNA markers and 10 genes. One of the genes used as a marker, SOX-9, we had previously mapped to the long arm of chromosome 17 (unpublished data, see legend to FIG. 8). The same markers were then tested on the somatic call hybrid B1, which was constructed by fusing mouse L cells with fibroblasts from E., a sex reversed CD patient. The hybrid B1 retains the human translocation chromosome 2pter-q35:17q23-qter in the absence of the reciprocal translocation chromosome and the normal chromosome 17 from the parent cell line. Chromosome 17 markers present in B1 must be located distal to the breakpoint (i.e. between the breakpoint and the end of the long arm of chromosome 17), while markers missing from the hybrid must be located proximal to the breakpoint. From this analysis, the microsatellite marker D17S970 was deduced to be the closest proximal marker to the breakpoint and the gene SOX-9 was found to be the closest distal marker (FIG. 6). Assuming an approximate distance of 20 Mb between GH and TK, the radiation hybrid map can be used to estimate the distance between D17S970 and SOX-9 as 1–2 Mb.

Construction of a YAC Contig and the Precise Localisation of the Translocation Breakpoint The markers flanking the translocation breakpoint were used to screen the ICRF (Lehrach, H. et al., 1990, in Genome Anslysis Volume 1: Genetic and Physical Mapping (eds.

Figure 7:
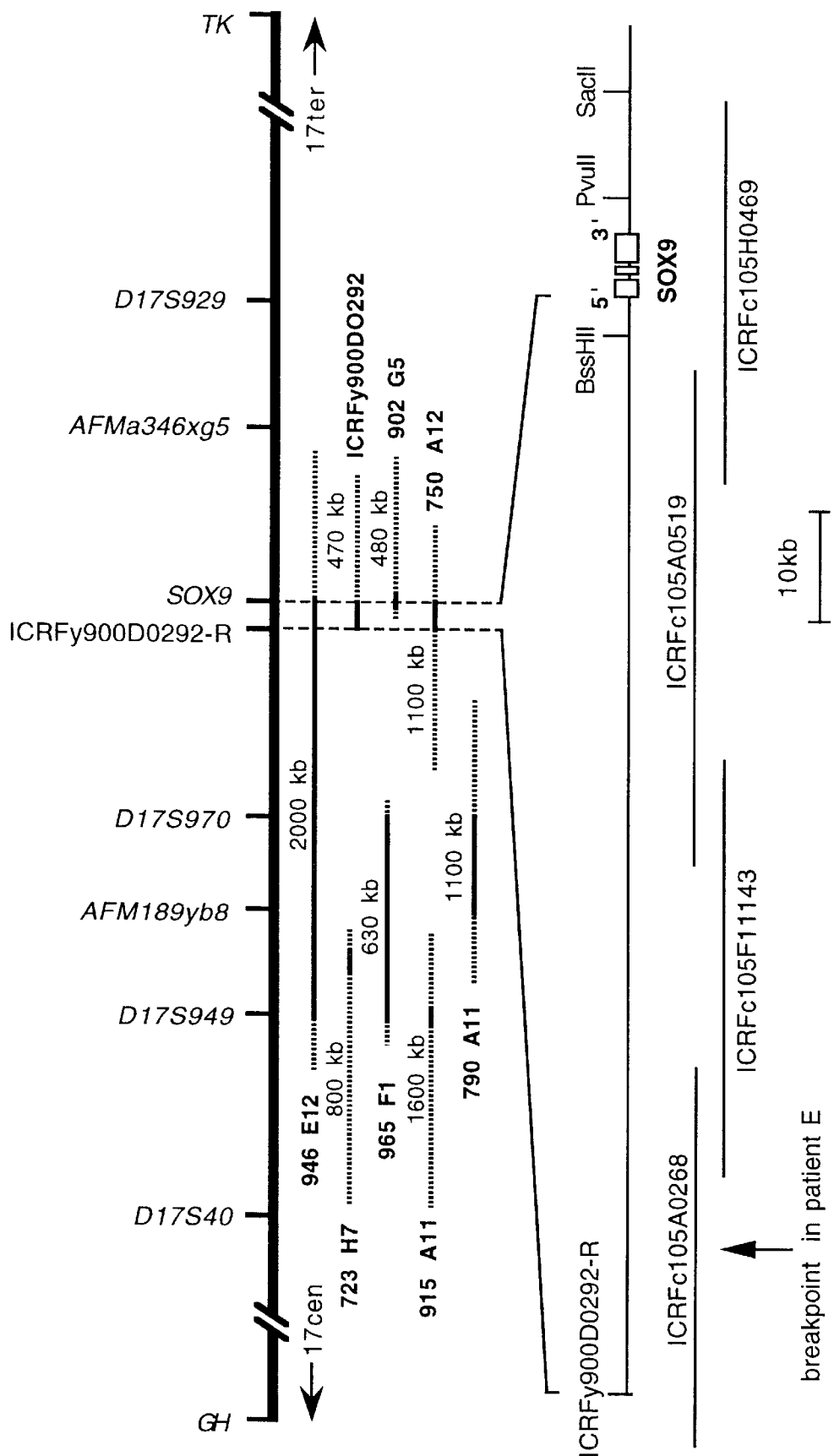

Davies, K. E. & Tilghman, S. H., pp 39–81. Cold Spring Harbor Laboratory Press, Cold Spring Harbor) and CEPH YAC libraries (Cohen. D. et al., 1993, J. Nature, 366, 698–701). One the flanking STS markers (D17S970) and an additional marker in this region (D17S949), had already ben used to screen the CEPH library as part of the Genethon and Whitehead/MIT Genome Center mapping projects. The YACs identified in these screens were sized, and a YAC contig was constructed based on STS content (FIG. 7). Probes from the ends of the YACs were isolated and tested back on hybrid B1 DNA as well as the other YACs to verify the contig. The ICRF YAC D0292, which was identified by the SOX-9 probe, yielded an end clone, D0292R, that failed to hybridise with hybrid B1 DNA. This result placed the translocation breakpoint in the region between SOX-9 and D0292R. Analysis of D0292 by pulsed-field gel electrophoresis determined that these markers were separated by 105–120 kb (data not shown).

A cosmid contig of the region between SOX-9 and D0292R was constructed by screening the ICRF chromosome 17 cosmid library (Lehrach, H. et al., 1990, supra) with Inter-Alu PCR products derived from one of the YACs (946 E12) which spans the region. Inter-Alu positive cosmids were tested with markers flanking the translocation breakpoint and these served as starting points for a cosmid walk. A contig was assembled using isolated cosmid ends to identify overlapping cosmids from the YAC Alu-PCR positive cosmid set (FIG. 7). The end clones were mapped back onto the hybrid B1 and one of these detected the breakpoint in Patient E and hybrid B1 on Southern blots of BamHI digested DNA (data not shown). The distance from the breakpoint to the SOX-9 open reading frame is 88 kb.

Characterisation of the SOX-9 Gene

Transcripts corresponding to the human SOX-9 gene were isolated as part of experiments aimed at identifying novel SOX genes by screening a testis cDNA library at high stringency with a SOXA HMG box probe (Stevanovic, M. et al., 1993, supra). The isolated cDNAs were identified as SOX-9 based on similarity to the published partial sequence containing the mouse Sox-9 HMG box region (Wright, E. M. et al., 1993, supra). We have assembled a composite transcript of 3934 bp using sequence obtained from cDNA clones isolated from three independent libraries (FIG. 8a (SEQ ID NO: 20)). Comparison of this sequence with the corresponding genomic DNA revealed the presence of two introns (FIGS. 8a and 8b), the boundaries of which have canonical splice site junctions. SOX-9 is the first SOX gene reported to contain introns; other SOX/Sox genes studied at the genomic level (SRY, SOX-3 and SOX-4 and Sox-4) are single exon genes (Sinclair, A. H. et al., 1990, supra; Stevanovic, M. et al., 1993, supra; Farr, C. J. et al., 1993, supra; Schilham, M. W. et al., 1993, Nucleic Acids Res., 21, 2009). The 3' region of the composite cDNA sequence contains a potential polyadenylation signal located 19 bp upstream from a terminal polyadenosine tract. The cDNA sequence diverges from the genomic sequence at the poly (A) tract, indicating that the cloned cDNA contains the 3' end of the SOX-9 transcript. The composite cDNA contains an open reading frame (ORF) with an HMG box and three potential start codons. Using the most 5' methionine as the translation start site, a polypeptide of 509 amino acids is predicted (FIG. 8a (SEQ ID NO: 21)). This methionine is located 125 bp downstream of an in-frame stop codon, strongly suggesting that the complete ORF is contained within the cloned cDNA sequences. Northern blot analysis using a SOX-9 cDNA probe detects a transcript of approximately 4.5 kb in total cytoplasmic RNA from adult testis, adult heart and foetal brain (data not shown). The discrepancy of approximately 600 bp between the cDNA sequence length and the transcript size seen in Northern blots can be accounted for by as yet unidentified 5' non-coding sequences and polyadenylation of the transcript. The SOX-9 protein HMG box domain at amino acids 104–182 shares 71% similarity with the SRY HMG box and the c-terminal third of the protein has a proline- and glutamine-rich region, similar to activation domains present in some transcription factors (Mitchell, P. J. et al., 1989, Science, 245, 371–378). DNA and protein sequence database searches and subsequent sequence alignment with the SOX-9 HMG box identified mouse Sox-9, Sox-8 and Sox-10 as the most related sequences at 100%, 98% and 93% predicted amino acid identity respectively. The same searches using sequences located outside the HMG box did not detect any significant matches in the databases apart from mouse Sox-9. The human and mouse predicted proteins share 96% identity and these differences are mostly due to conservative substitutions however there was a marginal reduction in amino acid identity between mouse SOX-9 and chicken SOX-9 (93.4% identity) and between human SOX-9 and chicken SOX-9 (93.4% identity).

Figure 9:
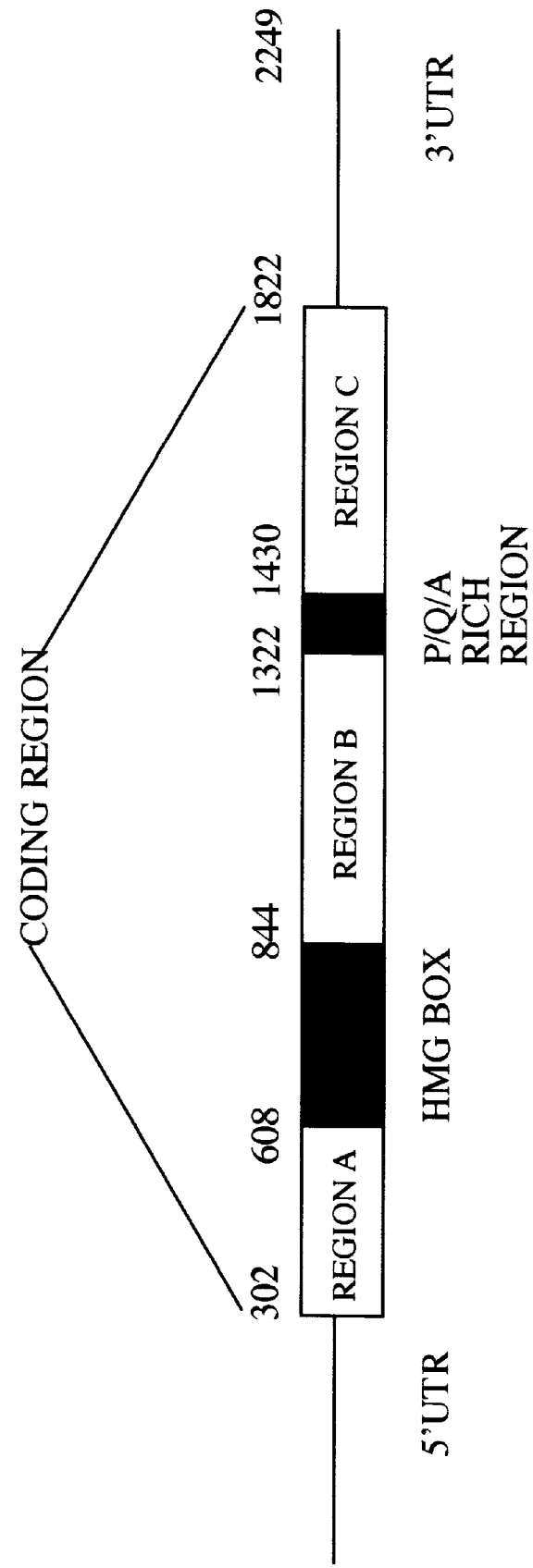

At the DNA level, sequence comparison between the respective predicted coding regions of the human SOX-9 gene and the mouse Sox-9 gene herein described reveals that these sequences share 91.3% identity. On the other hand, sequence comparison between these predicted coding regions and that of chicken Sox-9 (GenBank Accession No. U12533) indicates reduced identity at the DNA level (Mouse×Chicken: 79.3%; Human×Chicken: 82.4%). These data suggest that Sox-9 genes have higher identity within a class of vertebrates than between different classes. However, the coding regions can be subdivided respectively into several distinct sub-regions (See FIG. 9 illustrating the structure of mouse Sox-9). Amongst these is the HMG box (nt 608–843, FIG. 9), the highly conserved region that defines the Sox gene family (Goodfellow and Lovell-Badge, 1993, Annu. Rev. Genet., 27, 71–92); this region shows greater than 60% homology between all the members of the Sox gene family. Sequences outside this region give each Sox gene its individual character. Another region is a short stretch composed exclusively of proline (P), glutamine (Q) and alanine (A) reduces (nt 1322–1430, FIG. 9). Regions such as this are found in many genes, often associated with protein regions that act as transcriptional activators.

The remainder of the gene may be subdivided into three regions arbitrarily designated a, b, and c (FIG. 9). These regions are highly homologous between mouse Sox-9 and human SOX-9 (mammalian equivalents) (Table 1). Conversely, there is reduced homology between the respective mammalian regions and those of chicken Sox-9 (Table 1).

The very high degree of homology between mouse and human Sox-9 and the lack of other genes showing significant homology to Sox-9 enables a person skilled in the art to use these mammalian Sox-9 genes or parts thereof (preferably greater than 15 nt in length) as a means of generating other mammalian Sox-9 homologues using high stringency library screening (Sambrook et al., 1989, supra).

Initial localisation of SOX-9 using a monochromosomal somatic cell hybrid mapping panel, following by sublocalisation using chromosome 17 deletion hybrids mapped the gene to 17q23-qter (see FIG. 8 legend). This localisation was refined to 17q24 by fluorescence in situ hybridisation.

Mutation Analysis of SOX-9

The juxtaposition of SOX-9 and the translocation breakpoint in B1, as mapped using the radiation hybrid panel, prompted us to test for mutations in this gone in DNA samples from patients with clinically confirmed CD that do not have cytologically detectable chromosomal aberrations. Initial screening was performed using a single-strand conformation polymorphism (SSCP) assay. Primers were designed to amplify the known coding sequences and intro/exon junctions in overlapping fragments of approximately 150 bp. Fragments that gave altered SSCP patterns (unique SSCP conformers) were cloned into plasmid vectors and sequenced. Nine patent samples were investigated; these samples yielded six heterozygous mutations. We describe here three patients in detail.

Patient S.H. (46,XXfemale) (ECACC No. DD1813). This patient was delivered at full term with typical features of CD: micrognathia, hypoplastic scapulae, bilateral talipes equinovarus, hypoplastic cervical vertebrae, blowing of the long bones and eleven pairs of ribs. Cloning and sequencing of a unique SOX-9 SSCP conformer for this individual revealed a cytidine to thymidine base transition (nucleotide 583) that introduces a stop codon at amino acid position 195 of the predicted 509 amino acid sequence (FIG. 10). Both parents of this patient were screened by SSCP for this portion of SOX-9 and neither showed an aberrant shift (FIG. 10). In addition, DNA samples from over 100 unaffected individuals were screened by SSCP for this region of SOX-9. No anomalous shifts were seen in any normal individual. This is a de novo mutation.

Patient A.H. (46,XYfemale) (NIGMS No. GM01737). This sex reversed individual was delivered at term with a full spectrum of CD symptoms including short bowed limbs, small scapulae and characteristic facial features (Hoefnagel, D. et al., 1978, Clinical Genetics, 13, 489–499). Normal external female genitalia were present and the gonads were poorly differentiated with a substantial number of germ cells. Cloning and sequencing of the unique SSCP conformer for this patient (FIG. 10) identified a single G insertion in a series of six Gs (nucleotides 783–788) contained within codens 261–263 of SOX-9. The resulting frameshift introduces a premature stop codon such that a 294 amino acid protein would be translated, rather than the predicted normal 509 amino acid protein. Parental DNA of this patient could not be obtained. To investigate the possibility that this mutation occurs in unaffected individuals, SSCP was performed on this region of SOX-9 in more than 100 individuals without CD. No shifts corresponding to the Patient A.H. unique conformer were found.

Patient G. (46,XYfemale). Following ultrasound findings of short limbs and cystic hygroma, this foetus was aborted at 17 weeks. Clinical and radiological features include micrognathia, bowing of the limbs, hypoplastic scapulae, dislocated hips and eleven pairs of ribs. Normal female genitalia were present and the ovaries histologically appear normal with oocytes. The mutation found in the unique SSCP conformer from this patient was found to be the result of a four basepair insertion following amino acid 286 (nucleotide 858) of the predicted protein sequence (FIG. 8a). This frameshift introduces a premature stop at the same position as in patient A.H. SSCP analysis of this region of SOX-9 from both parents revealed a normal SOX-9 shift (FIG. 10). This is a de novo mutation.

We have used a positional cloning approach to define a breakpoint from a patient with both CD and autosomal XY sex reversal. The open reading frame of SOX-9, an SRY-related gene, is located 88 kb distal to the breakpoint on chromosome 17. We have found mutations in single alleles of SOX-9 in six of nine campomelic dysplasia patients examined. The three mutations described in detail here would be expected to destroy gene function: two mutations cause frameshifts which lead to premature chain termination and loss of one third of the protein and one mutation causes a premature termination that truncates the protein at 40% of its predicted length. Control populations of greater than 100 unaffected individuals were screened for two of these mutations and none were detected. SSCP analysis of both parents of two of the patients revealed the absence of the mutation present in their offspring. The de nova appearance of a mutation in a sex reversed CD patient establishes that alterations in SOX-9 can cause both campomelic dysplasia and autosomal sex reversal.

The precise relationship between the translocation breakpoint and SOX-9 is currently unclear. The SOX-9 transcript in adult testis, adult heart and foetal brain is approximately 4.5 kb, however, the cDNA isolated from testis, foetal brain and fibrosarcoma cDNA libraries cover 3.9 kb of the transcript, leaving approximately 600 bp of untranslated sequence unaccounted for. The genomic arrangement of SOX-9 is such that the 5' end is oriented towards the chromosome 17 centromere and closest to the breakpoint. It is possible that one or more exons are present 5' to the known exons and that these are disrupted by the translocation. Alternatively, the Translocation may disrupt expression by a more subtle mechanism, such as interfering with chromatin domains Dillon, N. et al., 1994, Current Opinion in Genetics and Development, 4, 260–264). Such long-range position effects have been demonstrated for Sry, where deletions of Y chromosomal material outside the minimal testis determining region can disrupt Sry expression and cause XY female sex reversal (Capel, B. et al., 1993, Nat. Genet, 5, 301–307). Other instances of genes affected by translocations located at a distance have been reported (Tommerup, N., 1993, J. Med. Genet., 30, 713–727). It is striking that several of the CD translocation patients have survived early childhood and the disease may be milder in these individuals (Mansour, S., 1994, MSc Thesis (Clinical Genetics), University of London).

Campomelic dysplasia has previously been described as an autosomal recessive or even X-linked disease, although a few cases are more consistent with a dominant disorder (Bianchine, J. W. at al., 1971, Lacet, 1, 1017–1018; Thurmon, T. F. et al., 1973, J. Ped., 83, 841–843; Lynch, S. A. et al., 1993, supra). Our results support the suggestion that CD is an autosomal dominant disease. We have not detected a mutation in both SOX-9 alleles of any patient, in spite of having performed SSCP across greater than 70% of the SOX-9 open reading frame. Although it is possible that a common null allele remains undetected, the frequency of this mutation would have to be improbably high to be found in our unrelated patients. The predicted loss of gene function in these mutants together with the absence of mutations in both alleles implies that the dominance is due to haploinsufficiency rather than gain of function. Dosage sensitivity is often a feature of regulatory genes and has been described for several sex determination systems including the mammalian pathway (Bardoni, B. et al., 1994, supra; Parkhurst, S. M. et al., 1994, Science, 264, 924–932).

A prediction for autosomal dominance of SOX-9 mutations is that deletions resulting in monosomy 17q should cause CD. Such deletions are very rare, presumably due to an associated lethality and have nearly always been reported associated with a ring chromosome. Interestingly, in a single reported 17q deletion not associated with a ring chromosome, the patient exhibited a number of physical features that occur in CD, including angulation of the lower limbs (Bridge. J. et al., 1985, Am. J. Med. Genet, 21, 225–229). Cases diagnosed as CD have a wide range and severity of associated phenotypes, including "acampomelic" campomelic dysplasia and the suggestion of long bone and short bone varieties (McKusick, V. A., 1992, supra). It will be of interest to determine the extent of SOX-9 Involvement in all cases diagnosed as CD. The heterogeneity and variability in clinical manifestations of constitutional bone disorders leaves open the possibility that SOX-9 is involved in other skeletal dysplasias.

By analogy with SRY, it has been suggested that SOX genes might act as transcription factors in developmental control pathways. Some SOX/Sox proteins have been shown to exhibit sequence-specific binding (Harley, V. R. et al., 1992, Science, 255, 453–456; Denny, P. et al., 1992, EMBO J, 11, 3705–3712; van de Wetering, M. et al., 1993, EMBO J. 12, 3847–3854) and the C-terminal third of the SOX-9 protein has a proline- and glutamine-rich region, similar to activation domains present in some transcription factors (Mitchell, P. J. et al., 1989, Science, 245, 371–378). This region would be missing in products translated from the mutated sequences present in the patients described in this report. The expression pattern of mouse Sox-9 is consistent with a role in regulating mesenchymal cell differentiation to chondrocytes as discussed above.

Mutations in SOX-9 causing male to female sex reversal in 46,XY individuals could be acting either before or after SRY in the sex determination pathway. The phenotype of 46,XY patients with mutations in SRY is usually female with complete gonadal dysgenesis. In a few cases, SRY mutations have been found to be inherited, with normal males and XY females occurring in the same family. These observations suggest that genes that perturb SRY function would result in either male or female, but probably no intersex development. Patients with CD show a spectrum of sexual phenotypes including partial masculinisation consistent with SOX-9 having a role subsequent to SRY in the sex determination pathway.

SOX-9 is not the first mammalian gene to be shown to have a dosage sensitive role in sex determination DSS causes male to female sex reversal, with varying degrees of masculinisation, when present in two copies in 46,XY individuals. Absence of DSS is compatible with male development in the presence of SRY but it is not known if it is compatible with female development in 46,XX individuals. Because of the importance of SOX-9 in bone formation, it is likely that nullisomy for SOX-9 is lethal. SOX-9 monosomy is compatible with ovarian development (Bridge, J. et al., 1985, supra) and trisomy for 17q, including the region containing SOX-9, has not been associated with sex reversal (Lenzini, E. et al., 1988, Ann. Genet, 31, 175–180). The cause of the variability of sex reversal associated with CD remains to be determined. There is no obvious correlation between the severity of the skeletal anomalies and the incidence of sex reversal (Mansour, S., 1994, supra). The presence or absence of sex reversal in XY individuals may be determined by the nature of the mutation, or could lie in allelic differences at other loci.

The dosage sensitivity of SOX-9 in sex determination and its sequence similarity to SRY suggest a possible evolutionary relationship between the two genes. It is plausible that a primordial dosage dependent sex determination system evolved into a dominant induction system by alteration of SOX-9 or another SOX gene (Foster, J. W., et al., 1994, supra). The mutated gene could function as a dominant inducer by becoming constitutively expressed and thus, when present, increasing dosage to be above a threshold required for male development.

There is a large body of indirect evidence suggesting that the sex determining function of SRY is expressed in pre-Sertoli cells in the developing gonadal ridge (Goodfellow, P. N. et al., 1993, Ann. Rev. Genet., 27, 71–92). SOX-9 could be required in these cells and SRY and SOX-9 interactions may be required for full cell function. Another possibility is that SOX-9 expression is required in a cell type that interacts with SRY-expressing pre-Sertoli cells to form testis. It is known that mesenchymal cells migrate from the mesonephros underlying the genital ridge and that these migratory cells are required for testis formation (Wheater, P. R. et al., 1979. Functional Histology (Churchill Livingstone, Edinburgh) and this might provide the link between CD and sex reversal. The identification of SOX-9 as a gene mutated in both CD and autosomal sex reversal provides new tools for studying bone formation and sex determination.

TABLE 1

Nucleotide homology of mouse, human and chicken Sox-9

| COM-PARISON | REGION A (nts 302–607) | REGION B (nts 844–1321) | REGION C (nts 1431–1822) | CODING REGION OVERALL |
|---|---|---|---|---|
| Mouse × Human | 94.8% | 90.0% | 90.8% | 91.3% |
| Mouse × Chicken | 85.4%* | 79.8% | 79.7% | 79.3% |
| Human × Chicken | 86.2%* | 84.5% | 81.5% | 82.4% |

TABLE 1

Figures shown are for nts 484–607 due to unavailability of full chicken sequence.
Numbers in parentheses indicate nucleotide positions in mouse Sox-9 sequence herein described.

What is claimed is:

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

AATTAAA                                                                         7

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

CCAAAGTCCT AAAGGTGGG                                                            19

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TTTCAGGCAA ATAAGGCAG                                                            19

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TGGCAATCTA ACAGATGAGA                                                           20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

TCNCAAATGT CATATATCCA                                                           20

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:6:

AGTCCAGATT GACTGGAACA CA                                                22

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GCAATAAGAT ACTAATATGT AGAG                                              24

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GTCAGCAGAA ATCCTAAAGG                                                   20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GACTAATGCC GATGGTTAAG                                                   20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CGCCTCGAGG TGGCTTATCG                                                   20

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

ATCATACACA TACGATTTAG GTGAC                              25

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GAGGAAGTCG GTGAAGAAC                                     19

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

TCGCTCATGC CGGAGGAGGA G                                  21

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GCAATCCCAG GGCCCACCGA C                                  21

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TTGGAGATGA CGTCGACTGC TC                                 22

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GCAGCGACGT CATCTCCAAC                                    20

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

| | |
|---|---|
| GCTGCTTGGA CATCCACACG T | 21 |

(2) INFORMATION FOR SEQ ID NO:18:

(i) SEQUENCE CHARACTERISTICS:
        (A) LENGTH: 2249 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

| | |
|---|---|
| AGTTTCAGTC CAGGAACTTT TCTTTGCAAG AGAGACGAGG TGCAAGTGGC | 50 |
| CCCGGTTTCG TTCTCTGTTT TCCCTCCCTC CTCCTCCGCT CCGACTCGCC | 100 |
| TTCCCCGGGT TTAGAGCCGG CAGCTGAGAC CCGCCACCCA GCGCCTCTGC | 150 |
| TAAGTGCCCG CCGCCGCAGC CCGGTGACGC GCCAACCTCC CCGGGAGCCG | 200 |
| TTCGCTCGGC GTCCGCGTCC GGGCAGCTGA GGGAAGAGGA GCCCCAGCCG | 250 |
| CCGCGGCTTC TCGCCTTTCC CGGCCACCCG CCCCCTGCCC CGGGCTCGCG | 300 |
| TATGAATCTC CTGGACCCCT TCATGAAGAT GACCGACGAG CAGGAGAAGG | 350 |
| GCCTGTCTGG CGCCCCCAGC CCCACCATGT CGGAGGACTG GCTGGTTCG | 400 |
| CCCTGTCCCT CGGGCTCCGG CTCGGACACG GAGAACACCC GGCCCCAGGA | 450 |
| GAACACCTTC CCCAAGGGCG AGCCGGATCT GAAGAAGGAG AGCGAGGAAG | 500 |
| ATAAGTTCCC CGTGTGCATC CGCGAGGCGG TCAGCCAGGT GCTGAAGGGC | 550 |
| TACGACTGGA CGCTGGTGCC CATGCCCGTG CGCGTCAACG GCTCCAGCAA | 600 |
| GAACAAGCCA CACGTCAAGC GACCCATGAA CGCCTTCATG GTGTGGGCGC | 650 |
| AGGCTGCGCG CAGGAAGCTG GCAGACCAGT ACCCGCATCT GCACAACGCG | 700 |
| GAGCTCAGCA AGACTCTGGG CAAGCTCTGG AGGCTGCTGA ACGAGAGCGA | 750 |
| GAAGAGACCC TTCGTGGAGG AGGCGGAGCG GCTGCGCGTG CAGCACAAGA | 800 |
| AAGACCACCC CGATTACAAG TACCAGCCCC GGCGGAGGAA GTCGGTGAAG | 850 |
| AACGGACAAG CGGAGGCCGA AGAGGCCACG GAACAGACTC ACATCTCTCC | 900 |
| TAATGCTATC TTCAAGGCGC TGCAAGCCGA CTCCCCACAT TCCTCCTCCG | 950 |
| GCATGAGTGA GGTGCACTCC CCGGGCGAGC ACTCTGGGCA ATCTCAGGGT | 1000 |
| CCGCCGACCC CACCCACCAC TCCCAAAACC GACGTGCAAG CTGGCAAAGT | 1050 |
| TGATCTGAAG CGAGAGGGGC GCCCTCTGGC AGAGGGGGGC AGACAGCCCC | 1100 |
| CCATCGACTT CCGCGACGTG GACATCGGTG AACTGAGCAG CGACGTCATC | 1150 |
| TCCAACATTG AGACCTTCGA CGTCAATGAG TTTGACCAAT ACTTGCCACC | 1200 |
| CAACGGCCAC CCAGGGGTTC CGGCCACCCA CGGCCAGGTC ACCTACACTG | 1250 |
| GCAGTTACGG CATCAGCAGC ACCGCACCCA CCCCTGCGAC CGCGGGCCAC | 1300 |

-continued

```
GTGTGGATGT CGAAGCAGCA GGCGCCGCCC CCTCCTCCGC AGCAGCCTCC          1350

GCAGGCCCCG CAAGCCCCAC AGGCGCCTCC GCAGCAGCAA GCACCCCCGC          1400

AGCAGCCGCA GGCACCCCAG CAGCAGCAGG CACACACGCT CACCACGCTG          1450

AGCAGCGAGC CAGGCCAGTC CCAGCGAACG CACATCAAGA CGGAGCAGCT          1500

GAGCCCCAGC CACTACAGGG AGCAGCAGCA GCACTCCCCG CAACAGATCT          1550

CCTACAGCCC CTTCAACCTT CCTCACTACA GGCCCTCCTA CCCGCCCATC          1600

ACCCGTTCGG AATACGACTA CGCTGACCAT CAGAACTCCG GCTCCTACTA          1650

CAGTCACGCA GCCGGCCAGG GCTCAGGGCT CTACTCCACC TTCACTTACA          1700

TGAACCCCGC GCAGCGCCCC ATGTACACCC CCATCGGTGA CACCTCCGGG          1750

GTCCCTTCCA TCCCGCAGAC CCACAGCCCG CAGGACTGGG AACAACCAGT          1800

CTACACACAG GTCACCAGAC CCTGAGAAGA GAAAAGCTAT GGTGACAGAG          1850

CTGATCTTTT TTTTTTTTT TTTTAAAGA AGAAAGAAA GAAACGAAAA             1900

AGAAAAAGCT GAAGGAAATC AAGAACCAAT TGAAATTCCT TTGGACACTT          1950

TTTTTTTTGT CCTTTCGTTA ATTTTTAAAA GACATGTAAA GGAAGGTAAC          2000

GATTGCTGGG CATTCCAGGA GAGAGACTTT AAGACTTTGT CTGAGCTCAT          2050

GACAACATAT TGCAAATGGC CGGGCCACTC GTGGCCAGAC GGACAGCACT          2100

CCTGGCCAGA TGGACCCACC AGTATCAGCG AGGAGGGGCT TGTCTCCTTC          2150

AGAGTTAACA TGGAGGACGA TTGGAGAATC TCCCTGCCTG TTTGGACTTT          2200

GTAATTATTT TTTAGCCGTA ATTAAAGAAA AAAAAGTCC AAAAAAAAA            2249
```

(2) INFORMATION FOR SEQ I D NO:19:

(i) SEQUENCE CHARACTERISTICS:
        (A) LENGTH: 507 amino acids
        (B) TYPE: amino acid
        (C) STRANDEDNESS: single
        (D) TOPOLOGY: linear (ii) MOLECULE TYPE:

(xi) SEQUENCE DESCRIPTION: SEQ ID NO:19:

```
Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
            20                  25                  30

Ser Pro Cys Pro Ser Gly Ser Gly Ser Asp Thr Glu Asn Thr Arg Pro
        35                  40                  45

Gln Glu Asn Thr Phe Pro Lys Gly Glu Pro Asp Leu Lys Lys Glu Ser
    50                  55                  60

Glu Glu Asp Lys Phe Pro Val Cys Ile Arg Glu Ala Val Ser Gln Val
65                  70                  75                  80

Leu Lys Gly Tyr Asp Trp Thr Leu Val Pro Met Pro Val Arg Val Asn
                85                  90                  95

Gly Ser Ser Lys Asn Lys Pro His Val Lys Arg Pro Met Asn Ala Phe
            100                 105                 110

Met Val Trp Ala Gln Ala Ala Arg Arg Lys Leu Ala Asp Gln Tyr Pro
        115                 120                 125

His Leu His Asn Ala Glu Leu Ser Lys Thr Leu Gly Lys Leu Trp Arg
    130                 135                 140
```

-continued

```
Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
            165                 170                 175

Arg Arg Arg Lys Ser Val Lys Asn Gly Gln Ala Glu Ala Glu Glu Ala
            180                 185                 190

Thr Glu Gln Thr His Ile Ser Pro Asn Ala Ile Phe Lys Ala Leu Gln
        195                 200                 205

Ala Asp Ser Pro His Ser Ser Gly Met Ser Glu Val His Ser Pro
210                 215                 220

Gly Glu His Ser Gly Gln Ser Gln Gly Pro Pro Thr Pro Pro Thr Thr
225                 230                 235                 240

Pro Lys Thr Asp Val Gln Ala Gly Lys Val Asp Leu Lys Arg Glu Gly
            245                 250                 255

Arg Pro Leu Ala Glu Gly Gly Arg Gln Pro Pro Ile Asp Phe Arg Asp
            260                 265                 270

Val Asp Ile Gly Glu Leu Ser Ser Asp Val Ile Ser Asn Ile Glu Thr
        275                 280                 285

Phe Asp Val Asn Glu Phe Asp Gln Tyr Leu Pro Pro Asn Gly His Pro
290                 295                 300

Gly Val Pro Ala Thr His Gly Gln Val Thr Tyr Thr Gly Ser Tyr Gly
305                 310                 315                 320

Ile Ser Ser Thr Ala Pro Thr Pro Ala Thr Ala Gly His Val Trp Met
            325                 330                 335

Ser Lys Gln Gln Ala Pro Pro Pro Pro Gln Gln Pro Pro Gln Ala
            340                 345                 350

Pro Gln Ala Pro Gln Ala Pro Pro Gln Gln Gln Ala Pro Pro Gln Gln
        355                 360                 365

Pro Gln Ala Pro Gln Gln Gln Ala His Thr Leu Thr Thr Leu Ser
        370                 375                 380

Ser Glu Pro Gly Gln Ser Gln Arg Thr His Ile Lys Thr Glu Gln Leu
385                 390                 395                 400

Ser Pro Ser His Tyr Arg Glu Gln Gln His Ser Pro Gln Gln Ile
            405                 410                 415

Ser Tyr Ser Pro Phe Asn Leu Pro His Tyr Arg Pro Ser Tyr Pro Pro
        420                 425                 430

Ile Thr Arg Ser Glu Tyr Asp Tyr Ala Asp His Gln Asn Ser Gly Ser
        435                 440                 445

Tyr Tyr Ser His Ala Ala Gly Gln Gly Ser Gly Leu Tyr Ser Thr Phe
450                 455                 460

Thr Tyr Met Asn Pro Ala Gln Arg Pro Met Tyr Thr Pro Ile Gly Asp
465                 470                 475                 480

Thr Ser Gly Val Pro Ser Ile Pro Gln Thr His Ser Pro Gln Asp Trp
            485                 490                 495

Glu Gln Pro Val Tyr Thr Gln Val Thr Arg Pro
            500                 505
```

(2) INFORMATION FOR SEQ ID NO:20:

(i) SEQUENCE CHARACTERISTICS:
        (A) LENGTH: 3923 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

```
CGGAGCTCGA AACTGACTGG AAACTTCAGT GGCGCGGAGA CTCGCCAGTT TCAACCCCGG        60
AAACTTTTCT TTGCAGGAGG AGAAGAGAAG GGGTGCAAGC GCCCCCACTT TTGCTCTTTT       120
TCCTCCCCTC CTCCTCCTCT CCAATTCGCC TCCCCCCACT TGGAGCGGGC AGCTGTGAAC       180
TGGCCACCCC GCGCCTTCCT AAGTGCTCGC CGCGGTAGCC GGCCGACGCG CCAGCTTCCC       240
CGGGAGCCGC TTGCTCCGCA TCCGGGCAGC CGAGGGGAGA GGAGCCCGCG CCTCGAGTCC       300
CCGAGCCGCC GCGGCTTCTC GCCTTTCCCG GCCACCAGCC CCCTGCCCCG GGCCCGCGTA       360
TGAATCTCCT GGACCCCTTC ATGAAGATGA CCGACGAGCA GGAGAAGGGC CTGTCCGGCG       420
CCCCCAGCCC CACCATGTCC GAGGACTCCG CGGGCTCGCC CTGCCCGTCG GGCTCCGGCT       480
CGGACACCGA GAACACGCGG CCCCAGGAGA CACGTTCCC CAAGGGCGAG CCCGATCTGA        540
AGAAGGAGAG CGAGGAGGAC AAGTTCCCCG TGTGCATCCG CGAGGCGGTC AGCCAGGTGC       600
TCAAAGGCTA CGACTGGACG CTGGTGCCCA TGCCGGTGCG CGTCAACGGC TCCAGCAAGA       660
ACAAGCCGCA CGTCAAGCGG CCCATGAACG CCTTCATGGT GTGGGCGCAG GCGGCGCGCA       720
GGAAGCTCGC GGACCAGTAC CCGCACTTGC ACAACGCCGA GCTCAGCAAG ACGCTGGGCA       780
AGCTCTGGAG ACTTCTGAAC GAGAGCGAGA AGCGGCCCTT CGTGGAGGAG GCGGAGCGGC       840
TGCGCGTGCA GCACAAGAAG GACCACCCGG ATTACAAGTA CCAGCCGCGG CGGAGGAAGT       900
CGGTGAAGAA CGGGCAGGCG GAGGCAGAGG AGGCCACGGA GCAGACGCAC ATCTCCCCCA       960
ACGCCATCTT CAAGGCGCTG CAGGCCGACT CGCCACACTC CTCCTCCGGC ATGAGCGAGG      1020
TGCACTCCCC CGGCGAGCAC TCGGGGCAAT CCCAGGGCCC ACCGACCCCA CCCACCACCC      1080
CCAAAACCGA CGTGCAGCCG GGCAAGGCTG ACCTGAAGCG AGAGGGCGC CCCTTGCCAG       1140
AGGGGGGCAG ACAGCCCCCT ATCGACTTCC GCGACGTGGA CATCGGCGAG CTGAGCAGCG      1200
ACGTCATCTC CAACATCGAG ACCTTCGATG TCAACGAGTT TGACCAGTAC CTGCCGCCCA      1260
ACGGCCACCC GGGGGTGCCG GCCACGCACG GCCAGGTCAC CTACACGGGC AGCTACGGCA      1320
TCAGCAGCAC CGCGGCCACC CCGGCGAGCG CGGGCCACGT GTGGATGTCC AAGCAGCAGG      1380
CGCCGCCGCC ACCCCCGCAG CAGCCCCCAC AGGCCCCGCC GGCCCCGCAG CGCCCCCGC       1440
AGCCGCAGGC GGCGCCCCCA CAGCAGCCGG CGGCACCCCC GCAGCAGCCA CAGGCGCACA      1500
CGCTGACCAC GCTGAGCAGC GAGCCGGGCC AGTCCCAGCG AACGCACATC AAGACGGAGC      1560
AGCTGAGCCC CAGCCACTAC AGCGAGCAGC AGCAGCACTC GCCCCAACAG ATCGCCTACA      1620
GCCCCTTCAA CCTCCCACAC TACAGCCCCT CCTACCCGCC CATCACCCGC TCACAGTACG      1680
ACTACACCGA CCACCAGAAC TCCAGCTCCT ACTACAGCCA CGCGGCAGGC CAGGGCACCG      1740
GCCTCTACTC CACCTTCACC TACATGAACC CCGCTCAGCG CCCCATGTAC ACCCCCATCG      1800
CCGACACCTC TGGGGTCCCT TCCATCCCGC AGACCCACAG CCCCCAGCAC TGGGAACAAC      1860
CCGTCTACAC ACAGCTCACT CGACCTTGAG GAGGCCTCCC ACGAAGGGCG ACGATGGCCG      1920
AGATGATCCT AAAAATAACC GAAGAAAGAG AGGACCAACC AGAATTCCCT TTGGACATTT      1980
GTGTTTTTTT GTTTTTTTAT TTTGTTTTGT TTTTCTTCT TCTTCTTCTT CCTTAAAGAC       2040
ATTTAAGCTA AAGGCAACTC GTACCCAAAT TTCCAAGACA CAAACATGAC CTATCCAAGC      2100
GCATTACCCA CTTGTGGCCA ATCAGTGGCC AGGCCAACCT TGGCTAAATG GAGCAGCGAA      2160
ATCAACGAGA AACTGGACTT TTTAAACCCT CTTCAGAGCA AGCGTGGAGG ATGATGGAGA      2220
ATCGTGTGAT CAGTGTGCTA AATCTCTCTG CCTGTTTGGA CTTTGTAATT ATTTTTTTAG      2280
```

```
CAGTAATTAA AGAAAAAAGT CCTCTGTGAG GAATATTCTC TATTTTAAAT ATTTTTAGTA      2340

TGTACTGTGT ATGATTCATT ACCATTTTGA GGGGATTTAT ACATATTTTT AGATAAAATT      2400

AAATGCTCTT ATTTTTCCAA CAGCTAAACT ACTCTTAGTT GAACAGTGTG CCCTAGCTTT      2460

TCTTGCAACC AGAGTATTTT TGTACAGATT TGCTTTCTCT TACAAAAAGA AAAAAAAAAT      2520

CCTGTTGTAT TAACATTTAA AAACAGAATT GTGTTATGTG ATCAGTTTTG GGGGTTAACT      2580

TTGCTTAATT CCTCAGGCTT TGCGATTTAA GGAGGAGCTG CCTTAAAAAA AAATAAAGGC      2640

CTTATTTTGC AATTATGGGA GTAAACAATA GTCTAGAGAA GCATTGGTA AGCTTTATGA       2700

TATATATATT TTTTAAAGAA GAGAAAAACA CCTTGAGCCT TAAAACGGTG CTGCTGGGAA      2760

ACATTTGCAC TCTTTTAGTG CATTTCCTCC TGCCTTTGCT TGTTCACTGC AGTCTTAAGA      2820

AAGAGGTAAA AGGCAAGCAA AGGAGATGAA ATCTGTTCTG GAATGTTTC AGCAGCCAAT       2880

AAGTGCCCGA GCACACTGCC CCCGGTTGCC TGCCTGGGCC CCATGTGGAA GGCAGATGCC      2940

TGCTCGCTCT GTCACCTGTG CCTCTCAGAA CACCAGCAGT TAACCTTCAA GACATTCCAC      3000

TTGCTAAAAT TATTTATTTT GTAAGGAGAG GTTTTAATTA AAACAAAAAA AAATTCTTTT      3060

TTTTTTTTTT TTTTCCAATT TTACCTTCTT TAAAATAGGT TGTTGGAGCT TTCCTCAAAG      3120

GGTATGGTCA TCTGTTGTTA AATTATGTTC TTAACTGTAA CCAGTTTTTT TTTATTTATC      3180

TCTTTAATCT TTTTTATTAT TAAAAGCAAG TTTCTTTGTA TTCCTCACCC TAGATTTGTA      3240

TAAATGCCTT TTTGTCCATC CCTTTTTTCT TTGTTGTTTT TGTTGAAAAC AAACTGGAAA      3300

CTTGTTTCTT TTTTTGTATA AATGAGAGAT TGCAAATGTA GTGTATCACT GAGTCATTTG      3360

CAGTGTTTTC TGCCACAGAC CTTTGGGCTG CCTTATATTG TGTGTGTGTG TGGGTGTGTG      3420

TGTGTTTTGA CACAAAAACA ATGCAAGCAT GTGTCATCCA TATTTCTCTA CATCTTCTCT      3480

TGGAGTGAGG GAGGCTACCT GGAGGGGATC AGCCCACTGA CAGACCTTAA TCTTAATTAC      3540

TGCTGTGGCT AGAGAGTTTG AGGATTGCTT TTTAAAAAAG ACAGCAAACT TTTTTTTTTA      3600

TTTAAAAAAA GATATATTAA CAGTTTTAGA AGTCAGTAGA ATAAAATCTT AAAGCACTCA      3660

TAATATGGCA TCCTTCAATT TCTGTATAAA AGCAGATCTT TTTAAAAAAG ATACTTCTGT      3720

AACTTAAGAA ACCTGGCATT TAAATCATAT TTTGTCTTTA GGTAAAAGCT TTGGTTTGTG      3780

TTCGTGTTTT GTTTGTTTCA CTTGTTTCCC TCCCAGCCCC AAACCTTTTG TTCTCTCCGT      3840

GAAACTTACC TTTCCCTTTT TCTTTCTCTT TTTTTTTTTG TATATTATTG TTTACAATAA      3900

ATATACATTG CATTAAAAAG AAA                                              3923

(2) INFORMATION FOR SEQ ID NO:21:

(i) SEQUENCE CHARACTERISTICS:
        (A) LENGTH: 509 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

Met Asn Leu Leu Asp Pro Phe Met Lys Met Thr Asp Glu Gln Glu Lys
 1               5                  10                  15

Gly Leu Ser Gly Ala Pro Ser Pro Thr Met Ser Glu Asp Ser Ala Gly
            20                  25                  30

Ser Pro Cys Pro Ser Gly Ser Gly Ser Asp Thr Glu Asn Thr Arg Pro
        35                  40                  45

Gln Glu Asn Thr Phe Pro Lys Gly Glu Pro Asp Leu Lys Lys Glu Ser
```

```
              50                  55                  60
Glu Glu Asp Lys Phe Pro Val Cys Ile Arg Glu Ala Val Ser Gln Val
 65                  70                  75                  80

Leu Lys Gly Tyr Asp Trp Thr Leu Val Pro Met Pro Val Arg Val Asn
                 85                  90                  95

Gly Ser Ser Lys Asn Lys Pro His Val Lys Arg Pro Met Asn Ala Phe
                100                 105                 110

Met Val Trp Ala Gln Ala Ala Arg Arg Lys Leu Ala Asp Gln Tyr Pro
                115                 120                 125

His Leu His Asn Ala Glu Leu Ser Lys Thr Leu Gly Lys Leu Trp Arg
                130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
                165                 170                 175

Arg Arg Arg Lys Ser Val Lys Asn Gly Gln Ala Glu Ala Glu Glu Ala
                180                 185                 190

Thr Glu Gln Thr His Ile Ser Pro Asn Ala Ile Phe Lys Ala Leu Gln
                195                 200                 205

Ala Asp Ser Pro His Ser Ser Gly Met Ser Glu Val His Ser Pro
210                 215                 220

Gly Glu His Ser Gly Gln Ser Gln Gly Pro Pro Thr Pro Pro Thr Thr
225                 230                 235                 240

Pro Lys Thr Asp Val Gln Pro Gly Lys Ala Asp Leu Lys Arg Glu Gly
                245                 250                 255

Arg Pro Leu Pro Glu Gly Gly Arg Gln Pro Pro Ile Asp Phe Arg Asp
                260                 265                 270

Val Asp Ile Gly Glu Leu Ser Ser Asp Val Ile Ser Asn Ile Glu Thr
                275                 280                 285

Phe Asp Val Asn Glu Phe Asp Gln Tyr Leu Pro Pro Asn Gly His Pro
                290                 295                 300

Gly Val Pro Ala Thr His Gly Gln Val Thr Tyr Thr Gly Ser Tyr Gly
305                 310                 315                 320

Ile Ser Ser Thr Ala Ala Thr Pro Ala Ser Ala Gly His Val Trp Met
                325                 330                 335

Ser Lys Gln Gln Ala Pro Pro Pro Pro Gln Gln Pro Pro Gln Ala
                340                 345                 350

Pro Pro Ala Pro Gln Ala Pro Pro Gln Pro Gln Ala Ala Pro Pro Gln
                355                 360                 365

Gln Pro Ala Ala Pro Pro Gln Gln Pro Gln Ala His Thr Leu Thr Thr
                370                 375                 380

Leu Ser Ser Glu Pro Gly Gln Ser Gln Arg Thr His Ile Lys Thr Glu
385                 390                 395                 400

Gln Leu Ser Pro Ser His Tyr Ser Glu Gln Gln Gln His Ser Pro Gln
                405                 410                 415

Gln Ile Ala Tyr Ser Pro Phe Asn Leu Pro His Tyr Ser Pro Ser Tyr
                420                 425                 430

Pro Pro Ile Thr Arg Ser Gln Tyr Asp Tyr Thr Asp His Gln Asn Ser
                435                 440                 445

Ser Ser Tyr Tyr Ser His Ala Ala Gly Gln Gly Thr Gly Leu Tyr Ser
                450                 455                 460

Thr Phe Thr Tyr Met Asn Pro Ala Gln Arg Pro Met Tyr Thr Pro Ile
465                 470                 475                 480
```

```
Ala Asp Thr Ser Gly Val Pro Ser Ile Pro Gln Thr His Ser Pro Gln
                485                 490                 495

His Trp Glu Gln Pro Val Tyr Thr Gln Leu Thr Arg Pro
            500                 505
```

1. An isolated DNA molecule comprising a sequence as set forth in SEQ ID NO: 18.

2. An isolated DNA molecule comprising a sequence as set forth in SEQ ID NO: 20.

3. An isolated DNA molecule comprising a sequence which codes for the protein of SEQ ID NO: 19.

4. An isolated DNA molecule comprising a sequence which codes for the protein of SEQ ID NO: 21.

* * * * *

UNITED STATES PATENT AND TRADEMARK OFFICE
CERTIFICATE OF CORRECTION

PATENT NO.    : 6,143,878
DATED         : November 7, 2000
INVENTOR(S)   : Peter A. Koopman et al.

It is certified that error appears in the above-identified patent and that said Letters Patent is hereby corrected as shown below:

Title page,
Item [56], OTHER PUBLICATIONS, "494" should read -- 495 --
Item [57], ABSTRACT,
Line 6, "bond" should read -- bone --

Column 1,
Line 16, "defects," should read --defects. --
Line 65, "5162" should read -- S162 --

Column 2,
Line 13, "tall" should read -- tail --
Line 45, "836)," should read -- 836). --

Column 3,
Line 15, "permatogenesis" should read -- spermatogenesis --

Column 4,
Line 65, "nap" should read -- map --

Column 5,
Line 38, "Invention" should read -- invention --

Column 7,
Line 2, "correspording" should read -- corresponding --

Column 9,
Line 61, "translocalion" should read -- translocation --

Column 10,
Line 54, "20$\geq$ 21" should read -- 20-21 --

Column 11,
Line 34, "shadring" should read -- shading --
Line 61, "681"should read -- 661 --
Line 67, "Elactrophoresis" should read -- Electrophoresis --

UNITED STATES PATENT AND TRADEMARK OFFICE
CERTIFICATE OF CORRECTION

PATENT NO. : 6,143,878
DATED : November 7, 2000
INVENTOR(S) : Peter A. Koopman et al.

It is certified that error appears in the above-identified patent and that said Letters Patent is hereby corrected as shown below:

Column 12,
Line 26, "The" should read -- the --
Line 33, "gone" should read -- gene --

Column 13,
Line 11, "Watering" should read -- Westering --

Column 15,
Line 17, "calls" should read -- cells --
Line 30, "specific" should read -- specific --

Column 16,
Line 46, "call" should read -- cell --

Signed and Sealed this

Twenty-eighth Day of January, 2003

JAMES E. ROGAN
*Director of the United States Patent and Trademark Office*